United States Patent
Blaine

(10) Patent No.: US 6,192,752 B1
(45) Date of Patent: Feb. 27, 2001

(54) NONINVASIVE ELECTROMAGNETIC FLUID LEVEL SENSOR

(75) Inventor: David Blaine, Salt Lake City, UT (US)

(73) Assignee: Zevex, Inc., Salt Lake City, UT (US)

(*) Notice: Subject to any disclaimer, the term of this patent is extended or adjusted under 35 U.S.C. 154(b) by 0 days.

(21) Appl. No.: 09/054,354

(22) Filed: Apr. 2, 1998

Related U.S. Application Data

(63) Continuation-in-part of application No. 08/831,205, filed on Apr. 2, 1997, now Pat. No. 6,023,970, which is a continuation-in-part of application No. 08/511,380, filed on Aug. 4, 1995, now Pat. No. 5,789,675.

(51) Int. Cl.[7] .................................................. G01F 23/00
(52) U.S. Cl. ........................................ 73/290 R; 73/61.44
(58) Field of Search .............................. 73/290 R, 290 V, 73/61.44, 1.22; 343/753; 324/640

(56) References Cited

U.S. PATENT DOCUMENTS

| | | | |
|---|---|---|---|
| 4,044,355 | * 8/1977 | Edwardsson | 343/14 |
| 4,054,255 | 10/1977 | Magenheim | 244/134 F |
| 4,069,710 | 1/1978 | Treier | 73/304 C |
| 4,083,038 | 4/1978 | Klebanoff | 340/244 R |
| 4,210,023 | * 7/1980 | Sakamoto et al. | 73/290 R |
| 4,280,126 | 7/1981 | White | 340/621 |
| 4,458,530 | * 7/1984 | Bastida | 73/290 R |
| 4,602,344 | * 7/1986 | Ferretti et al. | 364/509 |
| 4,631,529 | 12/1986 | Zeitz | 340/619 |
| 4,661,817 | * 4/1987 | Bekkadal et al. | 342/124 |
| 4,703,314 | 10/1987 | Spani | 340/619 |
| 4,749,988 | * 6/1988 | Berman et al. | 340/618 |
| 4,829,448 | 5/1989 | Balding et al. | 364/509 |
| 4,833,918 | 5/1989 | Jean et al. | 73/290 V |
| 4,901,245 | 2/1990 | Olson et al. | |
| 4,908,676 | 3/1990 | Bedell et al. | 356/72 |
| 4,920,336 | 4/1990 | Meijer | 340/619 |
| 4,984,462 | 1/1991 | Hass, Jr. et al. | 73/293 |
| 5,005,015 | 4/1991 | Dehn et al. | 340/962 |
| 5,015,995 | 5/1991 | Holroyd | 340/621 |
| 5,025,222 | * 6/1991 | Scott et al. | 324/639 |
| 5,112,319 | 5/1992 | Lai | 604/246 |
| 5,149,198 | * 9/1992 | Sterzer | 374/139 |
| 5,229,726 | 7/1993 | Kent | 324/632 |
| 5,233,319 | * 8/1993 | Mizan et al. | 333/219.1 |
| 5,254,992 | * 10/1993 | Keen et al. | 341/119 |
| 5,260,665 | 11/1993 | Goldberg et al. | 324/636 |
| 5,305,237 | * 4/1994 | Dalrymple et al. | 364/562 |
| 5,351,036 | 9/1994 | Brown et al. | 340/618 |
| 5,351,521 | * 10/1994 | Cracknell | 73/19.1 |
| 5,371,509 | * 12/1994 | Wallace, Jr. et al. | 343/741 |
| 5,406,842 | * 4/1995 | Locke | 73/290 R |
| 5,432,482 | * 7/1995 | Bailey | 331/56 |
| 5,437,184 | 8/1995 | Shillady | 73/304 C |
| 5,455,565 | 10/1995 | Moeenziai et al. | 340/603 |
| 5,473,245 | 12/1995 | Silvus, Jr. et al. | 324/207.13 |
| 5,475,350 | * 12/1995 | Yamada et al. | 333/223 |
| 5,485,743 | * 1/1996 | Taherian et al. | 73/61.4 |
| 5,789,675 | * 8/1998 | Blaine et al. | 73/290 R |
| 5,832,772 | * 11/1998 | McEwan | 73/290 R |

FOREIGN PATENT DOCUMENTS

WO97/06413   2/1997   (WO).

OTHER PUBLICATIONS

Seeger, John A. Microwave Theory, Components, and Devices, Prentice–Hall, New Jersey, 1986, pp. 220–222, 224–225, and 208–210.*

* cited by examiner

*Primary Examiner*—Hezron Williams
*Assistant Examiner*—Michael Cygan
(74) *Attorney, Agent, or Firm*—Morriss, Bateman, O'Bryant & Compagni

(57) ABSTRACT

A disposable sensor is disclosed for non-invasively detecting and characterizing a container's contents. By generating microwave frequency signals, electromagnetic fields are produced by a sensor and penetrate a container. The EM fields are analyzed in regards to how they are perturbed by the container contents. Analysis of the perturbed EM fields enables determination of content level, content purity, content density, content temperature, container pressure, and content conductivity.

53 Claims, 17 Drawing Sheets

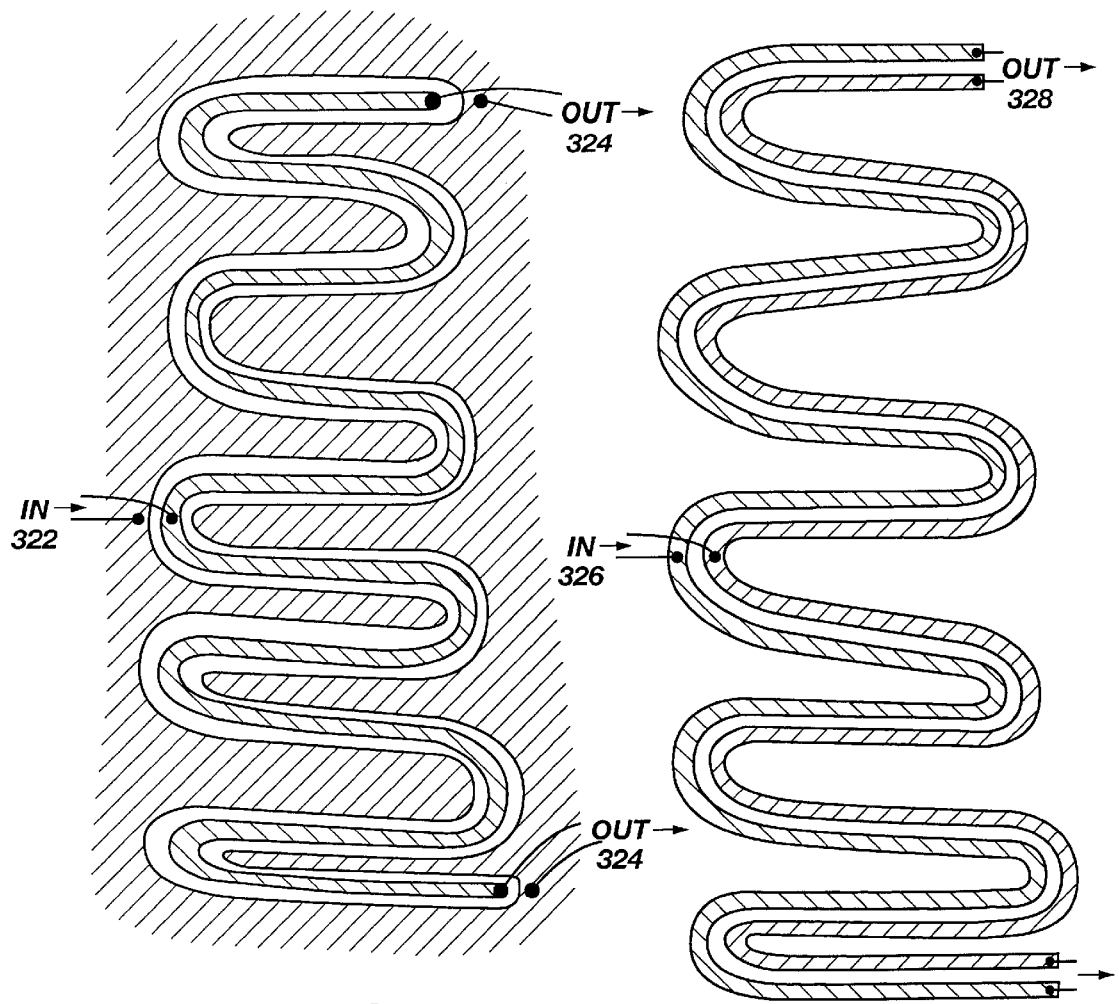
*Fig. 8O*
*Fig. 8P*
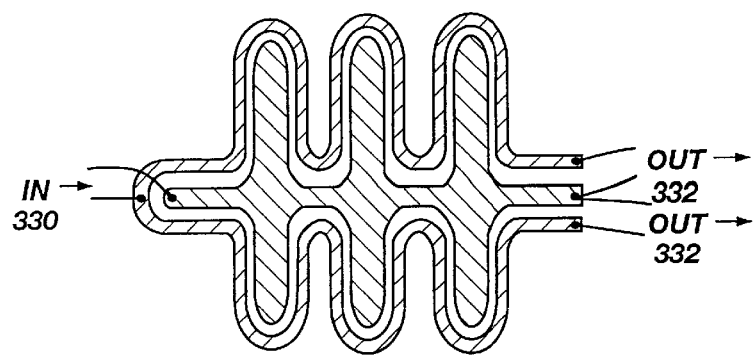
*Fig. 8Q*

NONINVASIVE ELECTROMAGNETIC FLUID LEVEL SENSOR

FILE HISTORY

This patent application is a continuation-in-part of U.S. patent application Ser. No. 08/831,205, U.S. Pat. No. 6,023,970, filed Apr. 2, 1997, which is a continuation-in-part of U.S. patent application Ser. No. 08/511,380, U.S. Pat. No. 5,789,675, filed Aug. 4, 1995.

BACKGROUND

1. The Field of the Invention

The present invention relates generally to non-invasive techniques for detecting and characterizing the contents of containers. More specifically, the invention relates to non-invasive measurement of materials within a container using microwave technology.

2. The State of the Art

Medical science often requires that liquids be administered to a patient in a variety of situations. These liquids include simple intravenous feeding solutions, saline solutions for providing pressure to the eye during ocular surgery, contrast media infused to enhance imaging abilities, blood administered during transfusions, and nutrient solutions delivered via an enteral feeding pump. In virtually all such situations, it could be dangerous for the liquid supply to inadvertently "run dry." In some applications, allowing the container to run dry may decrease the pressure of the liquid below that desired. In other situations, it can result in air entering the blood stream, causing complications or even death.

Several approaches have been suggested for monitoring containers of liquids so that inadvertent "running dry" can be avoided. For example, one system involves use of an electrical needle skewered into the bottom of a bottle containing liquid to be monitored. A constant electrical current is applied to the needle, and when the liquid level drops below the end of the needle, the break in the electrical current causes a lamp to light on a master control panel. A major disadvantage of this approach is that the fixed location of the needle results in a fixed triggering position. Thus, the user cannot select the liquid level at which the system will signal that the container needs to be refilled or replaced. And yet, the desired triggering position of the indicator may vary for different medical procedures. Additionally, some procedures may benefit from being able to vary the location at which the indicator signal reacts during different periods of the procedure.

An additional disadvantage of this system is that it is invasive. By placing the needle in the solution, the risk of contamination is increased.

Yet another disadvantage of such a system is that it is limited in the types of fluids which may be monitored therewith. For example, this system is designed to work with an ionic solution, but will not work with many solutions which are not ionic.

Other available systems have ultrasonic liquid level detectors for blood containers in which the transducer is placed against an exterior wall of the container. Ultrasonic signals are emitted into the container and reflected signals are used to determine when the liquid level has dropped below a designated point. The coupling between the transducer and container sidewall, however, requires that gel be placed on the sidewall to conduct the ultrasonic signals from the transducer into the container and from the container back into the transducer. This approach can be time consuming and messy as gel must be applied to the transducer or sidewall each time the two are coupled.

Other systems, such as that disclosed in U.S. Pat. No. 5,303,585, teach fluid volume sensors to determine the volume of gas or liquid within a container. However, the sensors transmit the signals to remote processing units which indicate to the user whether the volume of liquid is below the desired level.

All of these systems lack provision of a simple, noninvasive, inexpensive and disposable sensor which may be easily installed on the monitored container without cumbersome cables or coupling gel. Thus, there is a need for a simple, inexpensive and disposable sensor which may be quickly and conveniently applied to a container to be monitored.

A feature common to all of the sensor systems mentioned above is that the sensors are designed for placement on jars, bottles and containers which have rigid sidewalls. This limitation is due to the type of sensor being used. Specifically, the sensors are designed to detect signal reflections from the container sidewalls. The sensors also require reliable contact when mounted flush to the container to assure transfer of the majority of signal energy between the sensor and the container at all times.

Accordingly, there is a need for a sensor system which is versatile enough to accomplish liquid level detection, but which can also provide the capability of content characterization through analysis of signals. It would therefore be an advantage to be able to look at more than just reflected energy or energy loss from a sensor. While both of these energy signatures can provide useful information, it would be an advantage over the state of the art to generate electromagnetic fields which are perturbed or compressed, depending upon the nature of the container contents.

OBJECTS AND SUMMARY OF THE INVENTION

It is an object of the present invention to provide a sensor which is capable of non-invasively detecting contents of containers.

It is another object to provide a sensor which is capable of non-invasively detecting a level of a fluid within a container.

It is another object to provide a sensor which is capable of non-invasively detecting condensation on a container wall.

It is another object to provide a sensor which is capable of non-invasively measuring flow rates of a fluid within a fluid line.

It is another object to provide a sensor which is capable of non-invasively characterizing properties within a container, including material purity, material density, material temperature, container pressure, material conductivity, etc.

It is another object to provide a sensor which is capable of non-invasively detecting leakage from a container.

It is another advantage to provide a sensor system which uses direct analog driving of human perceptible alarms, or conversion of analog data to digital data, and then using indirect driving of the human perceptible alarms.

It is another object to provide a sensor system which takes advantage of various configurations of multi-port couplers to characterize a container's contents.

It is another advantage to provide a sensor system of multi-port couplers which enable sensing of differences of the same container contents at different locations within a same container.

It is another advantage to provide a sensor system which uses common mode rejection ratio data to modify sensitivity of the sensor to external factors which can affect sensor readings.

It is another object to provide a sensor system which forms a balanced bridge which uses constructive and destructive interference at a sensor output port.

It is another object to provide a sensor system which contains a memory of previous sensors readings of container contents so that a comparison can be made between past and present sensor readings to thereby detect changes in the contents.

It is another object to provide a sensor system which can measure various attributes simultaneously.

It is another object to provide a sensor system which is capable of pattern recognition.

These and other objects of the invention are realized in a sensor system which can be used as a liquid level indicator for determining the level of liquid in a container, which includes a sensor mechanism powered by an electric current, a means for mounting the sensor to a container, a processing module, and a means for transmitting signals between the processing module and the sensor. The sensor is mountable by adhesive which is integral to the sensor at selectable locations on the exterior of the container.

In a first aspect of the invention, the sensor system generates a level detection signal which is applied to the container at the level at which the sensor mechanism is positioned and which indicates whether or not fluid in the container is above or below the level of the sensor. In particular, the processing module generates a human perceptible signal indicating whether the fluid is present at the same level as the sensor mechanism. The exact positioning of the sensor mechanism on the container depends on the application for which the fluid in the container is used.

In a second aspect of the invention, the sensor system is capable of non-invasively detecting and characterizing a container's contents. By generating microwave frequency signals, electromagnetic fields are produced by a sensor and penetrate the container. The EM fields are analyzed in regards to how they are perturbed by the container's contents, the results of which enables characterization thereof.

In a third aspect of the invention, the advantages of different sensor coupler configurations are taught so that more information can be obtained regarding the container's contents.

These and other objects, features, advantages and alternative aspects of the present invention will become apparent to those skilled in the art from a consideration of the following detailed description taken in combination with the accompanying drawings.

BRIEF DESCRIPTION OF THE DRAWINGS

FIG. 8O is a profile view of a 3-port coupler consisting of a conductive stripline separated from a solid ground plane by a thin gap. The stripline forms a serpentine patterns to reduce the overall size of the sensor while maintaining the length of the stripline.

FIG. 8P is a profile view of a 3-port coupler consisting of two parallel serpentine striplines separated by a thin gap.

FIG. 8Q is a profile view of a 3-port coupler consisting of a stripline separated from the ground conductor by a thin gap.

DETAILED DESCRIPTION OF THE INVENTION

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

Before addressing the specific embodiments of the present invention, it is useful to present definitions for some words which will be presented herein. First, a container is any closed or open set of walls used to separate a sensor from a material being sensed. It is important that the container walls be composed of essentially non-conductive materials such as plastics, glass, fiberglass, ceramic, etc. It is also important that the walls be sufficiently thin to enable fringing fields of electromagnetic signals from the sensor to penetrate the walls and usually the contents as well. The container walls may be rigid or flexible, as well as flat, curved or of an irregular shape.

The contents being sensed within the container walls can be any type. However, most embodiments use as an example for illustrations purposes of fluid or fluid with air bubbles. The fluid is defined to be any contents which can flow or which might settle within a container. This fluid therefore includes solids (such as sand), liquids (such as blood), gasses (such as air), or any mixture thereof.

The present invention is a sensor which is designed to provide enhanced non-invasive container-content detection and characterization. It will become apparent that although the specific embodiments described hereinafter are directed to medical applications, the invention is also applicable to other contexts as will be explained.

Components of the present invention combine to provide an electromagnetic signal from a coupler adjacent to a container. Electromagnetic energy is either radiated into a liquid within the container if the liquid level is at or above the level where the coupler is attached, or is radiated into the air within the container if liquid is not present at the coupler location. By measuring coupled electromagnetic energy, it is then possible to determine if liquid is above or below the coupler location.

Figures 1, 2:
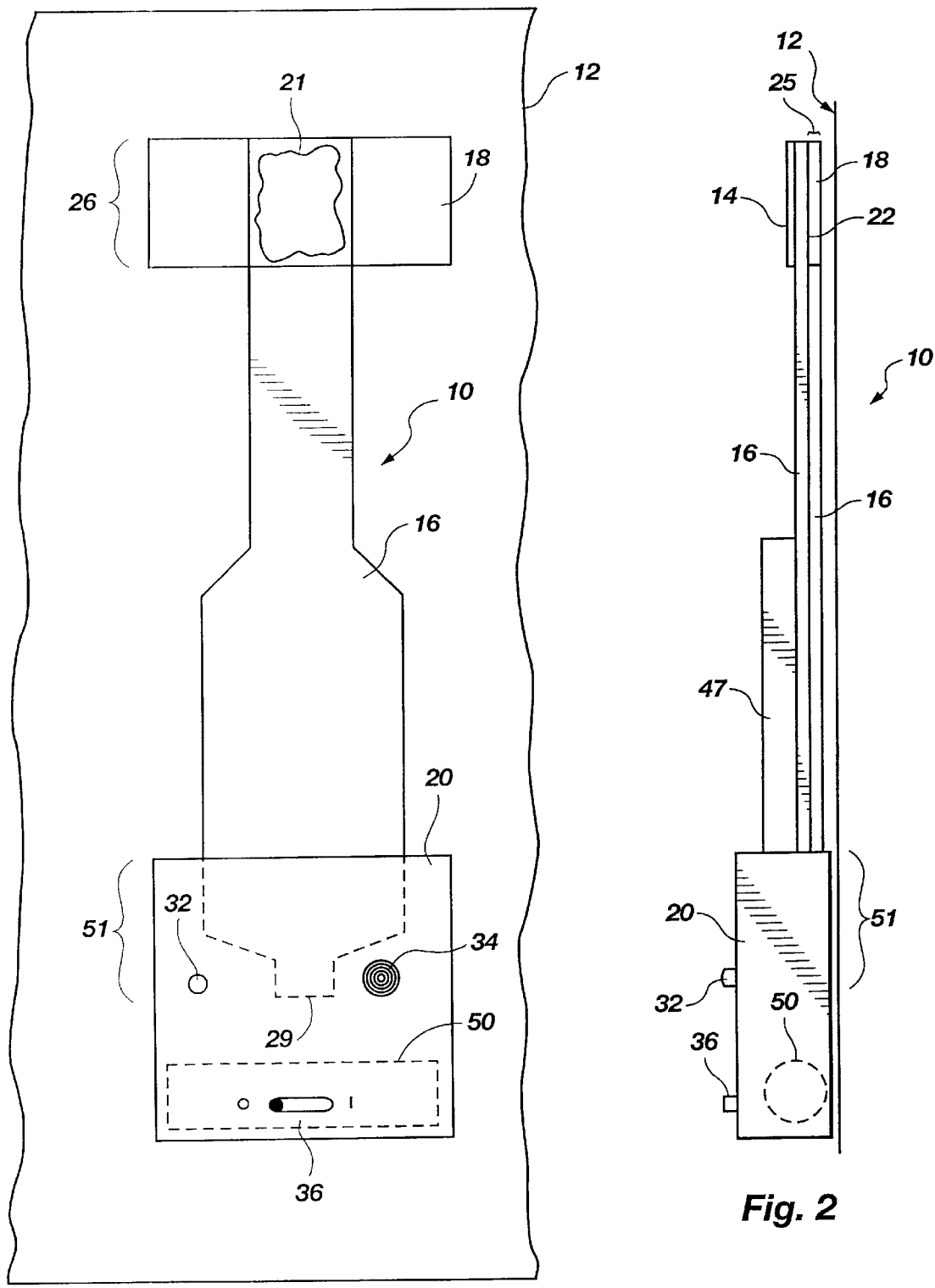
FIG. 1 shows a plan view of the disposable fluid level sensor with an accompanying processing module, made in accordance with the present invention.
FIG. 2 shows a side view of the disposable fluid level sensor with the accompanying processing module of FIG. 1.

FIG. 1 shows a non-invasive liquid level indicator 10 made in accordance with the present invention as it would be mounted to an exterior sidewall (plane of paper) of a container 12. The indicator 10 includes a flex circuit sensor 16, an integral adhesive patch 18, and a processing module 20.

The flex circuit sensor 16 couples to the integral adhesive patch 18 at a transmitting and receiving end 26. The adhesive patch 18 has an attachment surface 21 to which is applied an adhesive material. The adhesive material securely binds the attachment surface 21 to a front side of the flex circuit transmitting and receiving end 26 so as to provide a means of adhering/securing the sensor 16 to the container 12. The attachment surface 21 is sufficiently large so as to securely couple the flex circuit sensor 16 to a container 12.

The flex circuit sensor 16 also couples to the processing module 20 by a flex circuit edge connector 28 (FIG. 3) that slides into a friction coupling connector 29.

The processing module 20 includes a visual indicator means 32, such as a small light, and an audible indicator means 34, such as a speaker, to warn the user when the fluid in a container passes below the position of the transmitting and receiving end 26 of the flex circuit sensor 16. The processing module 20 also includes an on/off switch 36 to conserve power source 50 when the sensor 10 is not in use.

FIG. 2 is a profile view of the liquid level indicator 10 shown in FIG. 1. Distinct layers with exaggerated thicknesses of the flex circuit 16 are shown to clearly distinguish the various components of the invention. For example, while a gap 25 appears to indicate a substantial separation between the flex circuit transmitting and receiving end 26 and the container 12, it is only the scale of the drawing. The actual gap 25 is approximately 0.005 inches, which accommodates the adhesive patch 18. The nature of the flex circuit sensor 16 enables it to bend so as to be mounted flush against the container 12 with the adhesive patch 18.

A conductive patch 14 is placed on the flex circuit sensor 16 at the transmitting and receiving end 26. The conductive patch 14 is on the side of the flex circuit sensor 16 opposite the adhesive patch 18 and covers the entire transmitting and receiving end 26. Alternatively, the conductive patch 14 is fabricated as part of the flex circuit. The purpose of the conductive patch 14 is to electrically shield the transmitting and receiving end 26 in such a manner as to force the entire transmitted electromagnetic signal into the container 12. This prevents the flex circuit sensor 16 from detecting air on the backside of the transmitting and receiving end 26, and reduces interference from other electromagnetic energy sources.

Combined with the substrate of the flex circuit 16 is a nonconductive material 47 attached to a portion 51 of the flex circuit sensor 16 which slides into the processing module 20. The nonconductive material 47 is a support which stiffens the flex circuit sensor to give the flex circuit sensor 16 strength so as to not unduly bend and prevent a reliable contact when inserted in the processing module connector 29. When the liquid level indicator 10 is not in use, the on/off switch 36 can be moved into an off position to conserve power in the power source 50. Because the processing module 20 is not disposable, the power source 50 is stored within the processing module 20 so that the power source 50 is user replaceable. In a typical embodiment, the power source 50 would contain enough charge to enable the liquid level indicator 10 to function for about 50 hours in an "on" mode. It is envisioned that further refinement will show that the optimum power source 50 will likely be a lithium battery.

This figure also shows that the on/off switch 36 and the visual indicator means 32 extend slightly above an outward surface of the processing module 20. This feature makes the liquid level indicator 10 easier to turn on and off, and allows the visual indicator means 32 to be seen from a wider angle of view.

Figure 3:
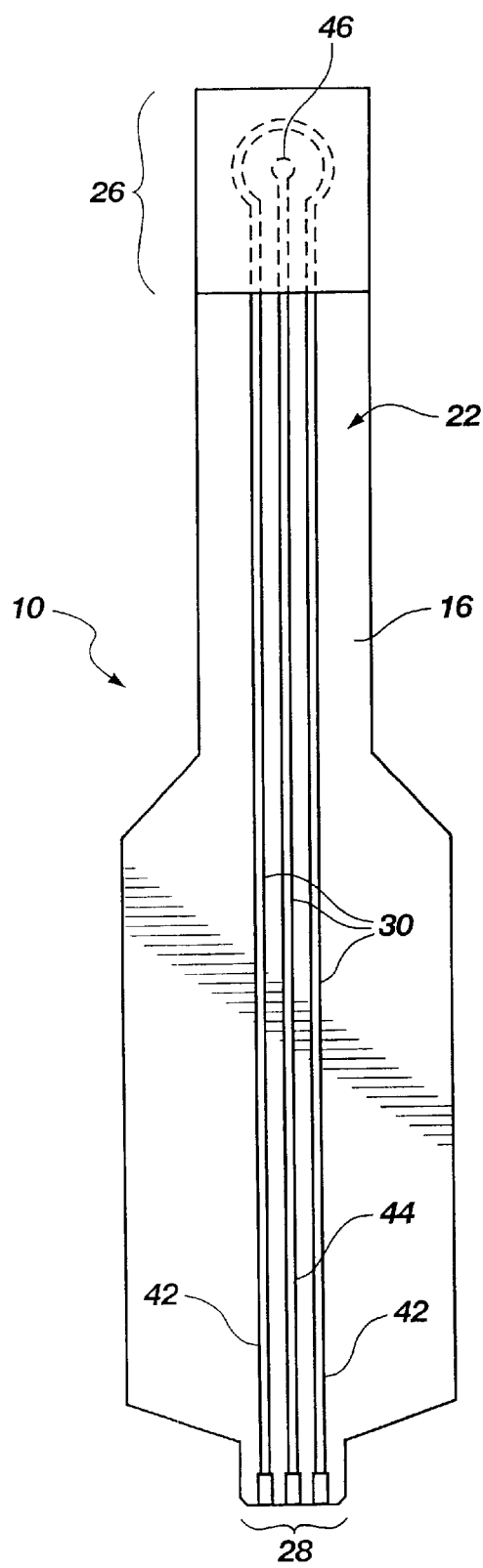
FIG. 3 shows a plan view of the flex circuit electromagnetic sensor of the present invention.
Figure 4:
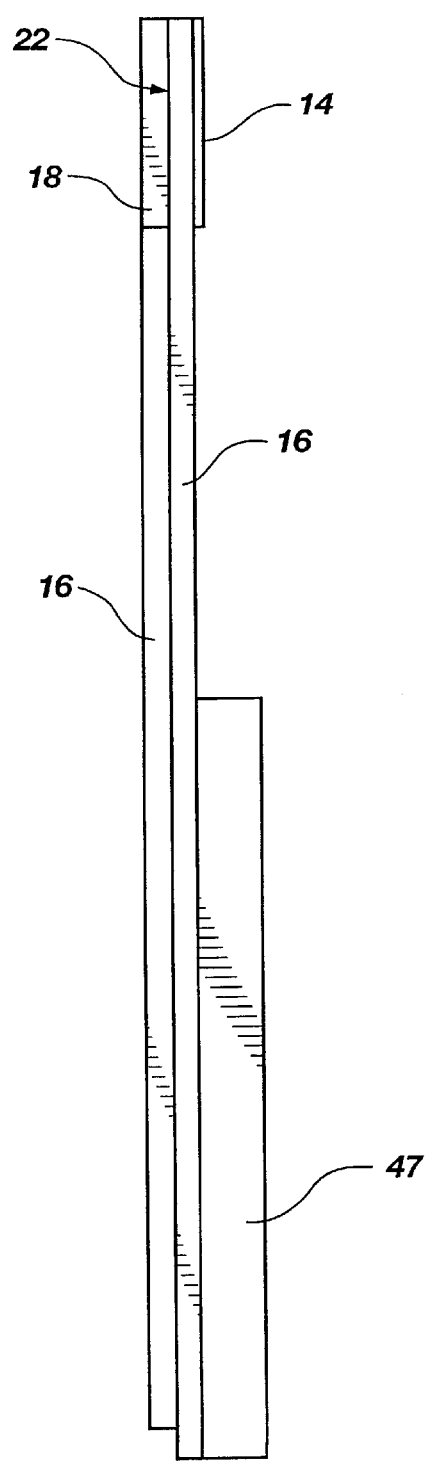
FIG. 4 shows a side view of the flex circuit shown in FIG. 3.

Referring now to the structure of FIGS. 3 and 4, there is shown a more detailed view of the flex circuit sensor 16 so as to illustrate the specific components of the flex circuit sensor. The flex circuit sensor 16 is oriented in FIG. 3 such that the surface 22 which faces a container sidewall is shown, without the processing module 20 attached to the flex circuit edge connector 28. Specifically, this view provides detail of the flex circuit traces 30, edge connector 28.

The flex circuit sensor 16 is designed to transmit and receive a signal from a transmitting and receiving end 26. An edge connector 28 is formed at the opposite end of the flex circuit 16 for coupling to the processing module 20 as previously described. The distance between flex circuit ends 26 and 28 is approximately 6 centimeters in a preferred embodiment, but could be longer or shorter. Copper traces 30 electrically couple the transmitting and receiving end 26 to the edge connector 28.

In a preferred embodiment, the circuit traces 30 are formed of copper with a thin layer of gold deposited thereon to prevent tarnishing of the copper surface. This gold layer also helps to ensure that the edge connector 28 makes a reliable electrical contact with the processing module friction connector 29.

As shown, the three copper traces 30 actually form only two distinct paths. The two outer traces 42 beginning at the edge connector 28 run parallel to the center trace 44, and form a circle around the center trace 44 at the transmitting and receiving end 26 of the flex circuit sensor 16. The center trace 44 has formed on an end 46 thereof a small copper disk 46.

Having described components of the present invention in detail, it is now possible to see how they provide the necessary structure and circuits to accomplish the objects of the invention. Specifically, the essence of the invention is to use a coupler which operates on the principle of radiating electromagnetic energy to different media and then measuring coupled energy. A full container 12 or one in which a fluid is above or at a position where the transmitting and receiving end 26 is currently attached couples almost no electromagnetic energy to the flex circuit sensor 16 of the present invention because electromagnetic energy broadcast by the flex circuit sensor 16 couples to the fluid within the container 12 and is perturbed and compressed.

On the other hand, if the container 12 is empty or there is no fluid in the container 12 at the position of the transmitting and receiving end 26, almost all of the electromagnetic energy is coupled back to the flex circuit sensor 16 because there is no fluid to couple with the energy and cause perturbation. Unlike an acoustic sensor where the timing between emission of a broadcast signal into a container and receipt of a return signal to the antenna is the critical parameter which indicates the presence of fluid, it is simply the presence or absence of coupled electromagnetic energy which is indicative of fluid in a container 12. Thus, if the fluid has passed below the position of the sensor transmitting and receiving end 26, there is coupling of a substantial portion of incident electromagnetic energy, and the liquid level indicator 10 alerts a user that the fluid in the container 12 has fallen below the level of the transmitting and receiving end 26 of the flex circuit sensor 16.

To obtain a reliable result from the liquid level indicator 10, the flex circuit sensor 16 must be securely attached to the sidewall of the container 12 by the adhesive patch 18 so as to ensure maximum transfer of electromagnetic energy emitted from the flex circuit sensor 16 to the coupled media, in this case the container 12 and possibly the fluid therein. Maximum electromagnetic energy transfer is crucial because the liquid level indicator 10 determines the level of liquid as a function of the magnitude and phase of electromagnetic energy coupled through the liquid near the sensor 16. A flex circuit sensor 16 held loosely against the container 12 is likely to result in a false indication that a liquid has fallen below the level of the transmitting and receiving end 26 of the flex circuit sensor 16.

While the type of adhesive material used to secure the liquid level indicator 10 to the container 12 is not a material element of the present invention, the use of adhesive results in the need to create a partially self-destructing flex circuit sensor 16. The adhesive patch 18 is sufficiently strong so as to be able to secure the flex circuit sensor 16 flush against the container 12 to ensure maximum electromagnetic energy transfer. However, such a strong adhesive is required to ensure maximum energy transfer that it is unlikely that the adhesive patch 18 could be reliably reattached to a container 12 once it is removed. If the flex circuit sensor 16 position must be changed on the container 12, a new disposable flex circuit sensor 16 must be applied at a new position, and the processing module 20 removed from the used flex circuit sensor 16 and coupled to a new flex circuit sensor.

To ensure that the flex circuit sensor 16 is not reused, it is designed to be unusable once the flex circuit 16 is pulled in sufficient tension to remove the adhesive. It is currently envisioned that a preferred embodiment is configured so that removing the flex circuit 16 will cause delamination of flex circuit copper traces 30, while leaving the adhesive patch 18 attached to the container 12. Such damage will force an operator to place a new flex circuit sensor 16 at a new location on the same container 12 because the flex circuit sensor 16 will be damaged and because the adhesive can no longer provide a reliable attachment to the container 12. Alternatively, the processing module 20 could produce an alarm signal indicative of the decoupling of the transmitting and receiving end 26 of the flex circuit sensor 16 from a container.

The processing module 20 contains the circuitry necessary to generate an electromagnetic signal to be transmitted from the flex circuit transmitting and receiving end 26, as well as to measure the amount of coupled energy after transmission by methods well known to those skilled in the art. When coupled energy changes sharply, the circuit activates the LED 32 and the speaker 34, alerting someone that the liquid level is below a predetermined level defined by the position of the transmitting and receiving end 26 of the flex circuit sensor 16 on the container 12.

The processing module 20 is also constructed of sufficiently small and lightweight materials so as to be light enough to hang suspended from the edge connector 28 without danger of decoupling. Such a material is impact resistant plastic. While the edge connector 28 is presently in tight sliding engagement with the friction coupling connector 29 of the processing module 20, any other connector which will enable the processing module 20 to hang from the flex circuit sensor 16 without pulling free by its own weight may be used. The flex circuit sensor 16 can be manufactured of any appropriate materials which enable the circuit to function as described above. In the preferred embodiment, the flex circuit 16 is constructed of a substrate composed of Kapton, polyamide or some other suitable plastic-like polyamide material. The formation of the traces 30 can be accomplished by numerous methods which will be apparent to those skilled in the art of forming flex circuits.

To further clarify use of the electromagnetic sensor, the flex circuit transmitting and receiving end 26 is firmly held against a sidewall 12 of the container by the adhesive patch 18. The processing module 20, powered by a power source such as a battery 50, sends an electromagnetic signal to the transmitting and receiving end 26 through the center trace 44. The flex circuit sensor 16 typically transmits an electromagnetic pulse in the range of 1 MHz to 10 GHz. It is believed, however, that refinement of the range to occur during further testing will result in an actual broadcast frequency of approximately 900 Mhz. Preferably, the antenna is a driven by a gated pulse signal of about 5 to 10 volts peak to peak in amplitude.

If the flex circuit sensor 16 has been properly applied to the container 12 and there is fluid within the container 12 above where the transmitting and receiving end 26 of the flex circuit sensor 16 is attached, a negligible amount of electromagnetic energy is coupled back to the flex circuit sensor 16. In response, any coupled electromagnetic energy is sent through the traces 42 and 44 to the processing module 20, where the signal is processed to determine the amplitude or phase or both of coupled energy. The processing module 20 actuates a visual indicator 32 and/or some other perceptible indicator, such as an audible indicator 34, to inform the user that the fluid level is adequate. Alternatively, the processing module 20 could be programmed or wired to not emit any indication signals until the liquid level passes below the transmitting and receiving end 26 of the flex circuit sensor 16.

The processing module 20 monitors the liquid level in a container 12 at least approximately 10 times per second. Consecutive responses are averaged to reduce the bit error rate and eliminate the influence of noise on the system. Upon receiving several consecutive negative responses, defined as a sharp change in coupled electromagnetic energy, the processing module 20 activates the alarm mechanisms.

The processing module 20 provides specific signals indicating the mode and status of operation. For example, the processing module 20 issues a single LED 32 pulse every five seconds to indicate a safe (high) liquid level indication. The module 20 issues an audible alarm through the speaker 34 consisting of four pulses in one second, repeated every five seconds, if there is an unsafe (low) liquid level indication. The LED 32 also blinks continuously at a rate of four times per second at a low liquid level condition. The module 20 also issues an audible alarm from the speaker 34 if the flex circuit sensor 16 is not within the vicinity of a detection media, or if the flex circuit sensor 16 is not properly connected to the processing module 20 when power is switched on.

When 50 hours of battery life have been expended, the liquid level indicator 10 provides an early warning audio alert to indicate a low battery condition. In a preferred embodiment, the audio warning alert consists of a single pulse repeated every 10 seconds. During this period of low battery alert, the sensor 10 continues to operate, including the single LED pulse repeated every 5 seconds. After approximately 30 minutes of low battery alert, an audio alarm sounds continuously at a rate of 4 pulses per second until the battery is completely expended. During this low battery alarm period, the LED 32 is completely off.

The motivation for creating this liquid level indicator 10 which uses electromagnetic signals is a desire to simplify operation of a liquid level sensor, and to create a more versatile sensor which may be used with both rigid and nonrigid containers while maintaining the same level of accuracy. It is believed that an electromagnetic liquid level indicator 10 accomplishes this simplification and versatility because for electromagnetic waves in the sub-gigahertz range, container wall thickness is much smaller than one wavelength. This means reflections off the outer wall surface of the container are approximately 180° out of phase with those off the inner wall surface The net effect is that the container is virtually invisible, and the reflected pulse magnitude depends only on the combined impedance of the coupler and the contents of the container. This is not true with ultrasound because the sonic wavelength is close to container thickness in many cases, and because acoustic impedances are such as to produce phase differences generally not close to 180°. This means reflections off the container dominate the processed signal, (i.e. the container is acoustically present). Ultrasonic sensing is, therefore, highly sensitive to container wall thickness, impedance and acoustic velocity.

Another advantage of this electromagnetic liquid level indicator 10 is that placement of the flex circuit sensor 16 is much simpler. No mounting projections are required to ensure that the flex circuit sensor 16 is oriented properly with respect to a container 12 and a reflected signal. It is only important that the flex circuit sensor traces 30 on the transmitting and receiving end 26 be flush against a container sidewall 12 so that transmitted electromagnetic energy is coupled to the attached container 12 resulting in variations in electromagnetic energy being coupled.

In addition to rigid wall containers such as glass balanced saline solution containers, this method for determining the level of liquid is also useful for thin walled plastic containers such as the containers used for blood, saline, medication and enteral feeding solutions. Unlike a glass container, the walls of a plastic container may collapse towards each other in an uncontrolled, random manner with a decrease in fluid volume within the container. Thus, the fact that the container can be flexible, or that a sidewall opposite to the attached container sidewall is not parallel to the coupled sidewall is no longer relevant to sensor accuracy or reliability with the present invention.

By applying the embodiment of the present invention and obvious modifications thereto, medical personnel can ensure that balanced saline solution and numerous other containers do not accidentally "run dry". The embodiment of the present invention can be used to detect air bubbles passing through medical tubing or non-metallic industrial hoses or piping, as it detects the presence and absence of liquid contained within the tubing. The embodiment can also be applied to numerous liquid level monitoring applications outside the medical environment, where accurate, low-cost liquid level monitoring on non-metallic tanks or vessels is desired.

The presently preferred embodiment of the present invention is a relatively small, lightweight and battery powered device consisting of a processing module and a sensor. There are mechanical and electrical connections between the processing module and the sensor.

There are several reasons why the preferred embodiment is a small, lightweight and battery operated device. First, it is a matter of convenience that the entire device be relatively small in comparison to the containers to which it is likely to be attached in medical applications. Accordingly, the container is typically a small bottle or bag being used to deliver medications or fluids to a patient.

Second, the sensor is preferably a single-use item. By providing a strong adhesive which ensures good contact between the sensor and the container, the chances of failure of the device are all but eliminated. This use of a strong adhesive also prevents re-use. However, given the low cost of the device and the desire to provide a sensor which will not detach accidentally, the single-use nature of the device is an asset. The adhesive is therefore strong enough to support the weight of the processing module as the device hangs from the container to which the sensor is attached.

Third, the ability to place the sensor at any location on the container enables the device to be adapted to specific user requirements.

It is mentioned before addressing the specific configuration of the preferred embodiment that the present invention is also capable of being integrated into larger systems such as a surgical console, heart-lung machine etc. What is important is that the device can be a portable and stand-alone device, and in this context the preferred embodiment will be explained.

Figure 5:
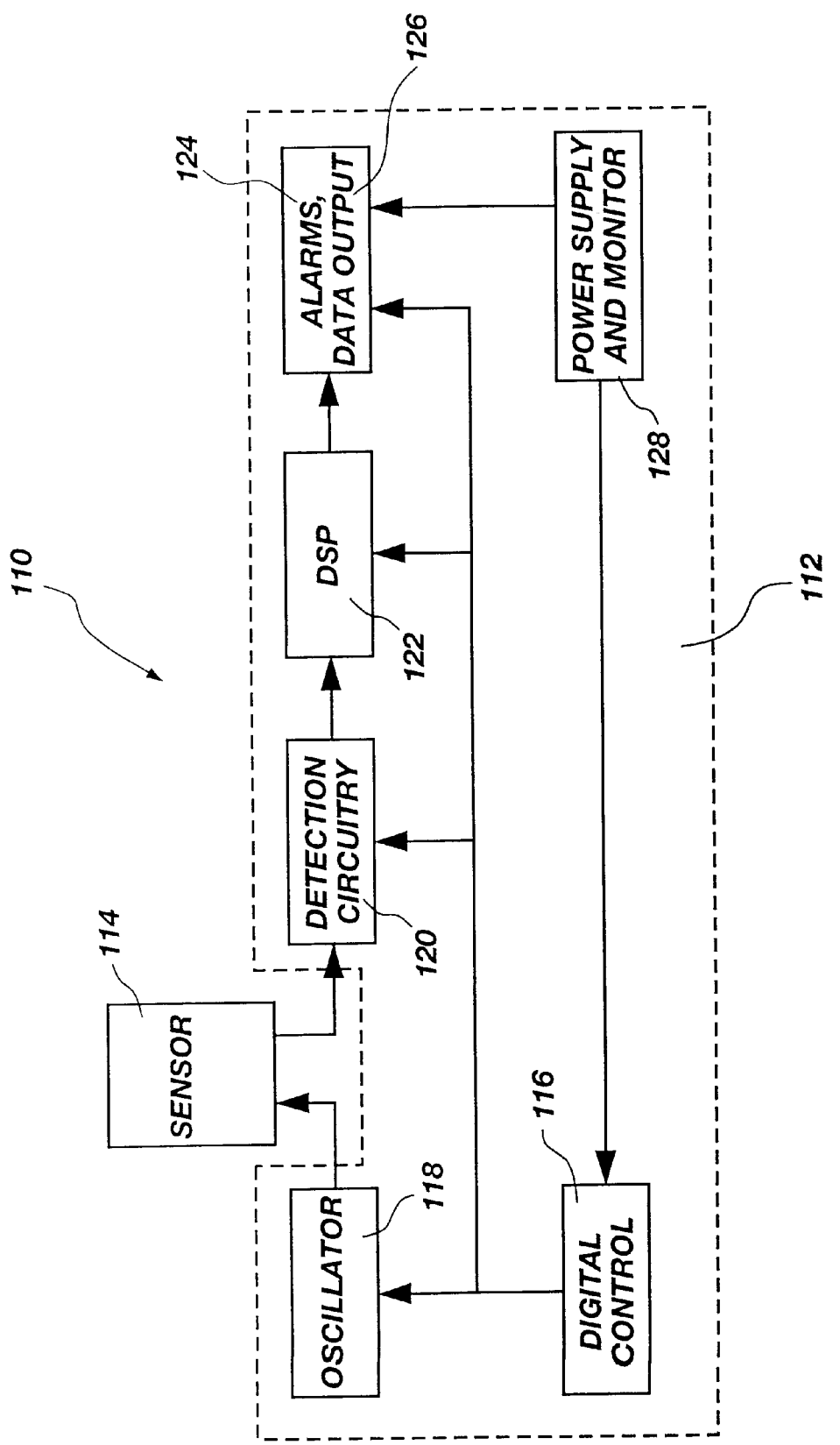
FIG. 5 is a block diagram which shows the components of the sensor system described in a preferred embodiment which is made in accordance with the principles of the present invention.

FIG. 5 is a block diagram of the elements which comprise the presently preferred embodiment. The sensor system 110 includes a processing module 112 and a sensor 114. The processing module 112 is preferably a digital device. A digital controller 116 operates to control all functions of the sensor system 110. These systems include an oscillator 118, detection circuitry 120, a digital signal processor (DSP) 122, an alarm system 124, a data port 126, and an integrated power supply and power supply monitor 128. It should be noted that the digital controller 116 is capable of sending commands to the oscillator 118, the detection circuitry 120, the DSP 122, the alarm system 124 and the data port 126.

When the sensor system 110 is operated as a stand-alone unit, it is advantageous to utilize power conservation techniques to thereby operate as long as possible without maintenance. In order to conserve battery life, the digital controller 116 activates microwave circuitry for only brief periods of time during which detection of the container's contents occurs. The microwave circuitry is then deactivated, or put in a sleep mode. During this sleep mode, very little battery power is used.

The duration of the activation period during the sleep mode period is advantageously configurable according to the user's specific needs. For example, when the sensor system 110 is being used to detect air bubbles in a fluid line, the sleep mode period will be much shorter in comparison to when the system 110 is being used to detect a fluid level in a container.

Of course, there are many factors which can influence the length of the activation and sleep mode periods. These factors are all related to the time sensitivity of the data. It is likely that detection of all air bubbles is critical. Furthermore, air bubble detection is also likely to occur in a tube where fluid can flow relatively swiftly, so data changes rapidly. In contrast, fluid level detection is likely to occur in a container in which change occurs much slower. However, a rate of fluid flow from a container can be varied, and thus a programmable sensing vs. sleep mode period is advantageous to the adaptability of the invention.

It is also important to recognize that while the preferred embodiment is sensitive to power requirements, this is not a critical factor when the sensor system 110 is integrated in larger systems of alternative embodiments. In these conditions where power consumption is not a factor, the sleep mode period can be reduced to zero seconds without concern, and regardless of the nature of the rate of data change.

The digital controller 116 can be programmed using any appropriate method. For example, the digital processor 116 might be a microprocessor or microcontroller with on-board memory, a programmable gate array, or programmable memory such as an EPROM (erasable programmable read only memory). In these devices, the program is typically described as residing in firmware. As such, the firmware can be changed by replacement of the programming instructions, or replacement of the device itself (such as swapping out the EPROM). Replacement of the instructions is accomplished by removing the device, erasing the previous instructions, burning in the new instructions, and placing the same device back into the sensor system 110.

The programming instructions can also reside in software. Accordingly, the memory device which stores the instructions must be capable of overwriting or remotely erasing and then writing the new instructions. The device is typically one which utilizes RAM (random access memory). RAM is updated in the presently preferred embodiment using a computer which is external to the sensor system 110. However, it should be apparent that flash memory (requiring erasure before writing to the memory) could also be used and programmed externally from the computer. A physical connection between the sensor system 110 and the external computer occurs through the data port 126.

The oscillator 118 provides a desired operating frequency of the sensor 114. In the context of the presently preferred embodiment, the sensor 114 is capable of generating an electromagnetic signal at a frequency in the range of 1 to 100 GHz.

It is advantageous to select a microwave oscillator which strikes a reasonable balance between cost and performance. This balance may be affected by the particular application for which the sensor system 110 will be used. For example, high resolution sensing of container contents requires an oscillator with good frequency and phase stability. In contrast, for liquid level detection, probably any tuned oscillator will provide sufficiently accurate results.

Figure 6:
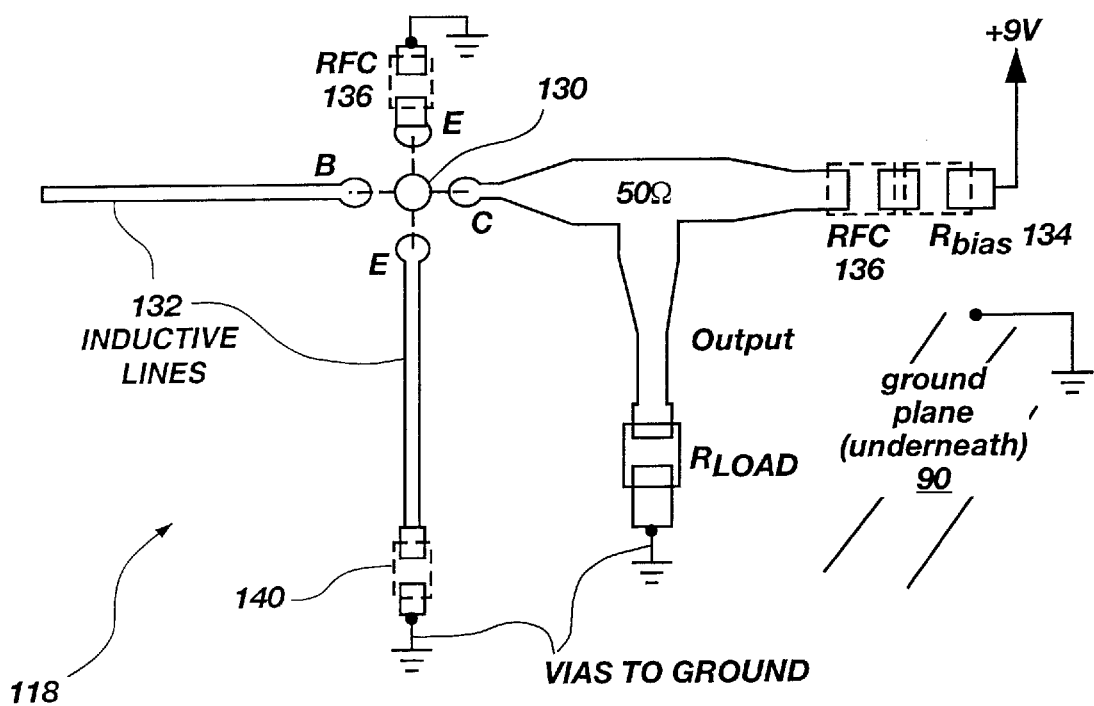
FIG. 6 is a schematic of a circuit diagram which shows the preferred embodiment of an oscillator which is used in the present invention to provide a microwave frequency signal.

FIG. 6 is a schematic view of an oscillator 118 which is used in the presently preferred embodiment. The microwave oscillator shown is a common-base bipolar gallium-arsenide transistor 130 having feedback through microstrip lines 132 and a capacitor 140. The frequency of the oscillator 118 is controlled by varying the length of the microstrip lines 132 and the value of the capacitor 140, as is known to those skilled in the art.

The output impedance of the oscillator 118 is matched to the input impedance of the sensor 114 to thereby obtain maximum power transfer from the oscillator 118 to the sensor 114. In this example, the output impedance of the oscillator is shown as 50 ohms.

The transistor 130 has DC biasing provided through a current limiting resistor R(bias) 134 and a microwave blocking inductor 136. The microwave blocking inductor 136 is also referred to as a radio frequency choke (RFC).

The output power and the oscillation frequency of the oscillator 118 is fine tuned by controlling bias current to the transistor 130. A field effect transistor 138 (not shown) driven by the digital controller 16 controls current from the power supply 128 to the transistor 130. In the preferred embodiment, the power supply 128 is a nine volt battery, but this can be modified. The nine volt battery was selected for its small size and because in typical operation, the current drain on the battery will be relatively small. Accordingly, the nine volt battery should provide power for adequate durations of time.

By providing bias current through the transistor 138, the transistor activates the oscillator 118 when the sensor 14 is to be in operation, and deactivates the oscillator 118 in order to enter the sleep mode period. These operations all occur under the direction of the digital controller 116. It should be apparent to those skilled in the art that the specific circuitry designed to provide power to the oscillator in order to drive the sensor 114 can also be implemented in other ways. It is also noted that in this presently preferred embodiment, a ground plane 90 is provided for grounding of circuit components.

The sensor 114 receives input directly from the oscillator 118. The input is in the form of a microwave frequency radio signal which is transmitted along the sensor's circuit as will be described later. In the presently preferred embodiment, the sensor circuit is a microwave device commonly known as a coupler. Ordinarily, couplers are used in microwave circuits as filters, signal mixers, signal splitters, tuners, matching networks, and for other functions known to those skilled in the art. It is believed that the use of a microwave coupler for determining characteristics of the contents of a container is a substantially new application of microwave sensing technology. A coupler provides a controlled electromagnetic connection from one circuit to another. The degree of connection versus isolation is controlled by many parameters including electromagnetic propagation modes within the coupler.

The type or configuration of microwave coupler which can be used as the sensor 114 in the present invention includes two-port couplers, three-port couplers, and four-port couplers. These microwave multi-coupler configurations can also be used in direct coupling and parallel coupling arrangements. In effect, the present invention can function properly using any coupler which is fabricated in generally planar surfaces. This includes couplers fashioned as concentric stripline rings as will be described.

Figure 7A:
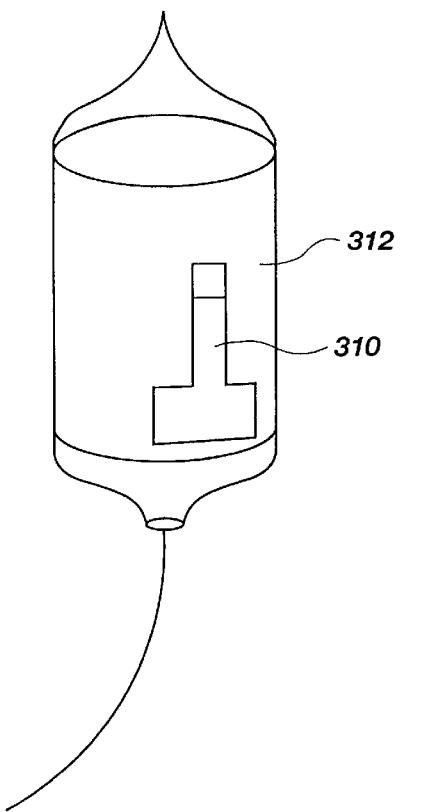
FIG. 7A is a perspective view of a sensor coupled to a bottle.
Figure 7B:
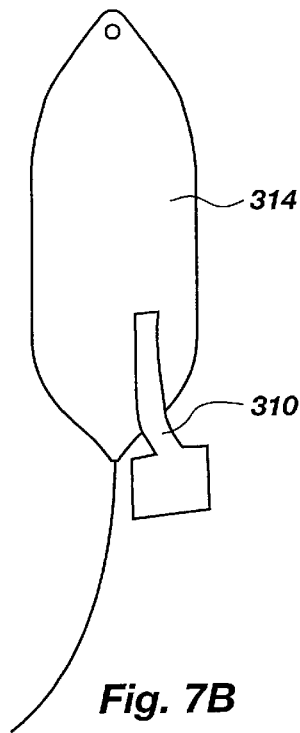
FIG. 7B is a perspective view of a sensor coupled to a collapsible bag.
Figure 7C:
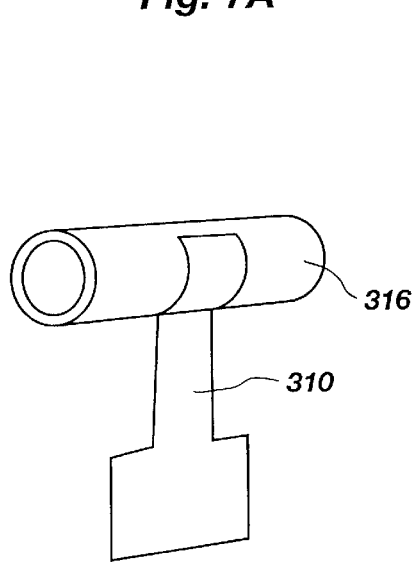
FIG. 7C is a perspective view of a sensor coupled to a tube.
Figure 7D:
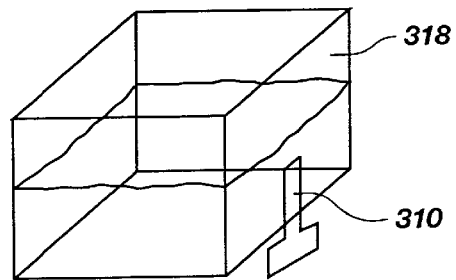
FIG. 7D is a perspective view of a sensor coupled to a tank.
Figure 7E:
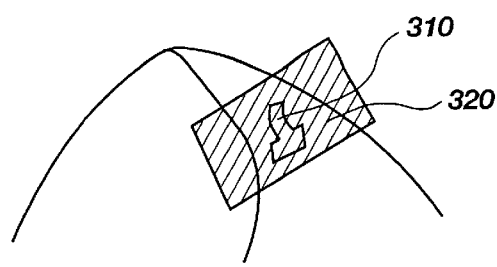
FIG. 7E is a perspective view of a sensor coupled to a sheet covering a mound of material.

In FIGS. 7A through 7E in the interest of context, the following figures are provided to show how the sensor appears when coupled to a container. The figures are intended to show that the sensor is attached to the container, and the circuitry hangs down below the sensor in some sort of housing to protect the components. The figures which are shown are also provided to demonstrate only a few of the many types of containers to which the sensor can be attached. FIG. 7A shows a sensor 310 coupled to a bottle 312 which contains intravenous fluids. FIG. 7B shows the sensor 310 attached to a collapsible bag 314 which also contains intravenous fluids. FIG. 7C shows the sensor attached to a section of tube, hose or pipe 316. FIG. 7D shows the sensor 310 attached to a tank 318 of fluid. Finally, FIG. 7E shows the sensor 310 attached to a sheet 320 for detection of bulk contents or proximity sensing.

Figure 8A:
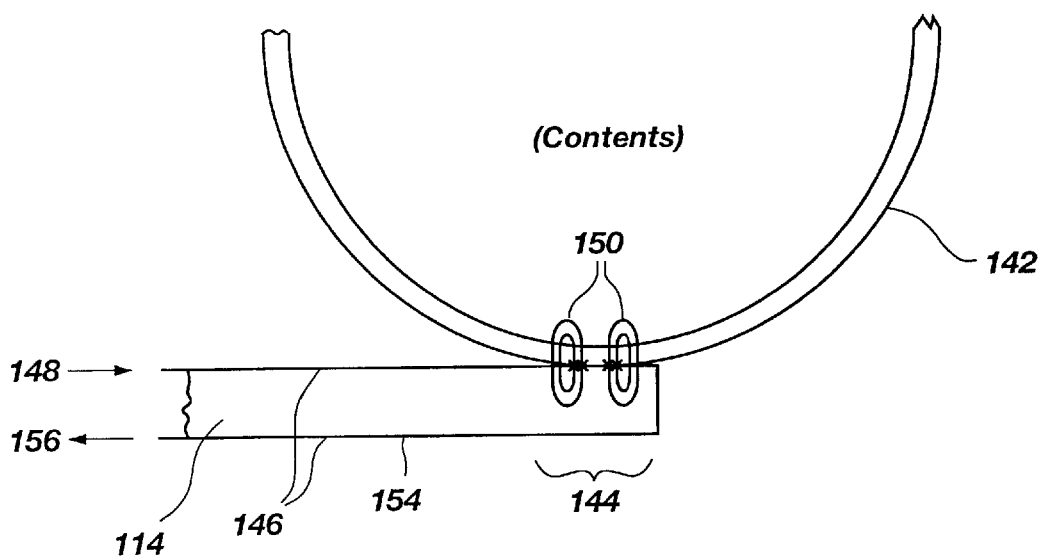
FIG. 8A is a top cut-away view of a container and a sensor attached to the container wall.
Figure 8B:
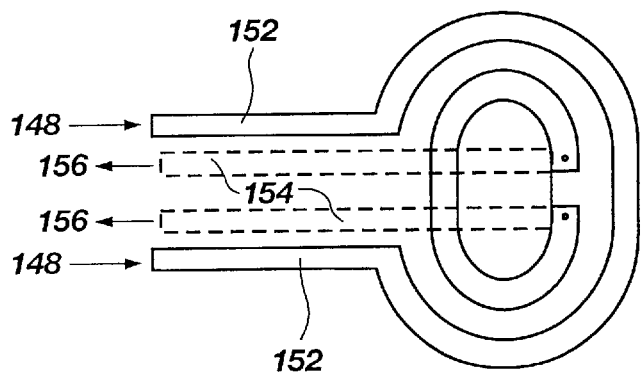
FIG. 8B is an enlarged profile view of the sensor shown in FIG. 8A.

FIG. 8A is a cross-sectional top view of a sensor 114 which is constructed as shown in an elevational view in FIG. 8B. However, the scale of FIG. 8B does not exactly match that of FIG. 8A. FIG. 8A shows the sensor 114, as well as an arcuate portion of a container wall 142. The portion 144 of the sensor 114 which is in contact with the container wall 142 generates EM (electromagnetic) fields 150 which are used in the content determination process. When seen from above, it is noticed that an input signal 148 to the portion 144 of the sensor 114 which is in contact with the container wall 142 is carried by striplines 146.

A stripline is a circuit trace configuration that is characterized by strips of conductors on an insulating substrate, thereby providing an input path 152 and an output path 154 for the microwave frequency signal 148. The width, length, thickness, material and orientation of the conductors and substrate are engineered as integral parts of electronic circuits. In the embodiments of the present invention, striplines may be of any quasi-planar shape and are disposed on any insulating surfaces of a substrate. In comparison, it is noted that micro-striplines are a stripline configuration in which conductors are placed on one side of a planar substrate and an essentially solid conductor plane on the other side of the substrate. The solid plane is the return path for the signals carried on the conductors. This geometry creates a nearly transverse electromagnetic (TEM) propagating field mode, as opposed to striplines in general which usually create a non-TEM field.

As shown, the EM fields 150 of the sensor 114 extend through the container wall 142, and usually penetrate the contents. Of course, this is a generalization in that it is assumed that the EM fields 150 are sufficiently strong enough to touch the contents.

The contents of the container will perturb or cause disruption in the EM fields 150. What is important to realize is that different contents will perturb the EM fields 150 in various ways. This is a result of the properties of the contents being detected. For example, non-magnetic non-conductive contents will cause electric fields to compress to a greater density than would otherwise occur in air. In contrast, ferrous contents will greatly compress the magnetic fields. Of course, conductive contents will essentially prevent the EM fields 150 from penetrating at all. It is this consequence of different materials causing different perturbations in the EM fields 150 which enables the present invention to accomplish determination of presence or absence of contents, as well as purity, density, pressure and temperature. However, this list should not be considered all-inclusive.

While the input signal 148 is sent to the sensor 114 via the input path 152, it is analysis of an output signal 156 from the output path 154 which enables container content determination. More specifically, the output signal represents the input signal 148 which is scaled to a specific degree, in accordance with the material properties of the contents. Thus, measurement of the output signal 156 can be used to accurately identify and even determine specific properties of the contents.

The EM fields 150 which surround the sensor 114 (also referred to as a coupler) support many "hybrid" coupling modes. For detailed analysis, these hybrid coupling modes are typically decomposed into many pure coupling modes that add up constructively and/or destructively at the coupler's output. Because analysis of many pure coupling modes is an involved process, it is possible to characterize a coupler by defining a coupling coefficient which is, in general, a complex number to represent the overall degree of coupling due to geometry and material properties of the coupler.

For example, the coefficient can be quantified as:

Equation 1:

$$c = \left(10 \log\left|\frac{p(\text{in})}{p(\text{out})}\right|, \varnothing(\text{out}) - \varnothing(\text{in})\right)$$

With known input power p(in) and input phase Ø(in), it is possible to measure output power p(out) and output phase Ø(out) to thereby determine the coupling coefficient while the coupler's EM fields are perturbed by the contents.

Before proceeding with a description of other components of the invention, it is useful to present some common coupler configurations using striplines and which can be used in the present invention. These couplers should only be considered examples of possible embodiments, and not as being an exclusive list of the only possible configurations.

Figure 8C:
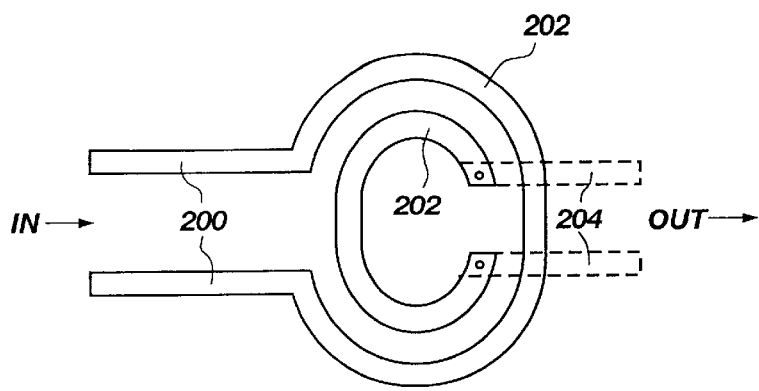
FIG. 8C is a profile view of a 2-port coupler which has input and output paths on opposite sides of a substrate.
Figure 8D:
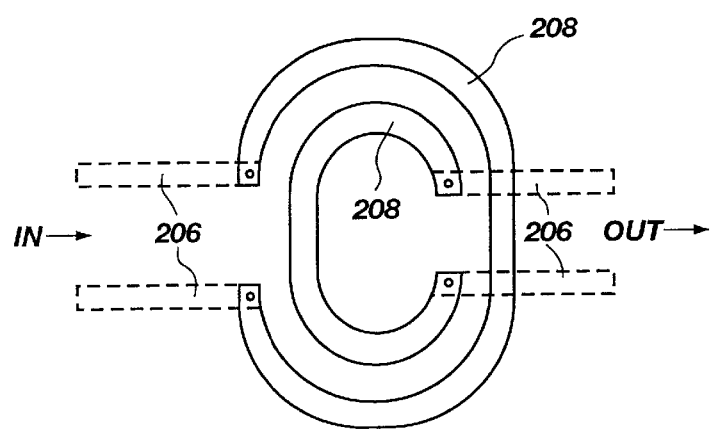
FIG. 8D is a profile view of a 2-port coupler which has input and output paths on a same side of the substrate.
Figure 8E:
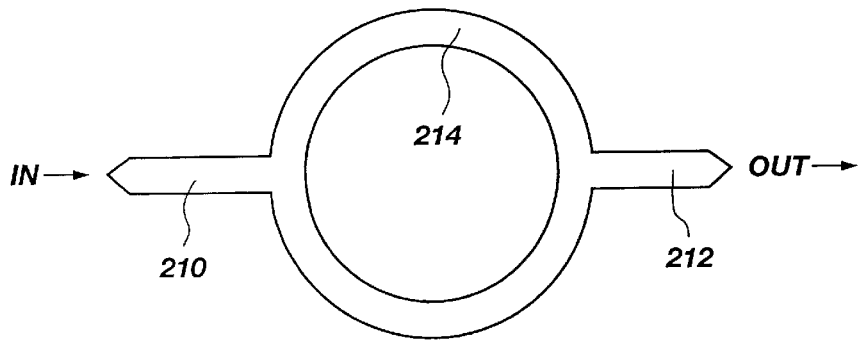
FIG. 8E is a profile view of a 2-port coupler which has a single input and output path, on a same side of a substrate, and where the input and output paths are electrically coupled.

FIGS. 8C, 8D and 8E are all embodiments of 2-port couplers. A sensor area is generally described as being formed from striplines which are shaped as rings. These rings do not have to be circles. FIG. 8C shows a 2-port coupler which has input striplines 200 on the same side of a substrate (not shown) as the sensor rings 202, and which has output striplines 204 on an opposite side of the substrate. FIG. 8D varies in that the input and the output striplines 206 are on a same side of a substrate (not shown) and on an opposite side of the substrate as the ring sensors 208. Finally, FIG. 8E shows an input 210 which is electrically coupled to an output 212 because they share a common sensor ring 214.

Figure 8F:
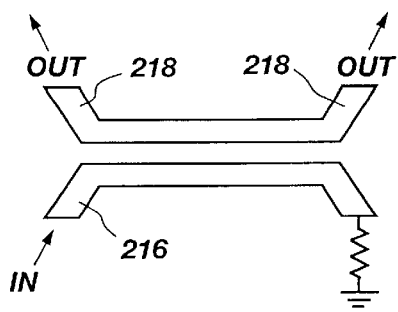
FIG. 8F is a profile view of a 3-port coupler.
Figure 8G:
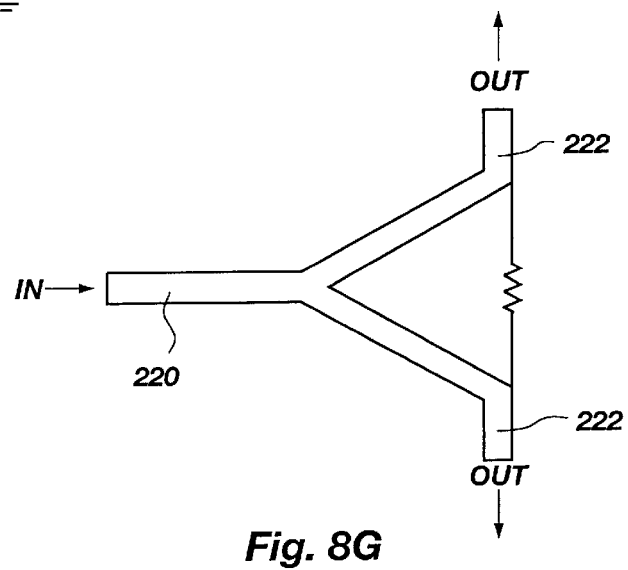
FIG. 8G is a profile view of a different 3-port coupler.
Figure 8H:
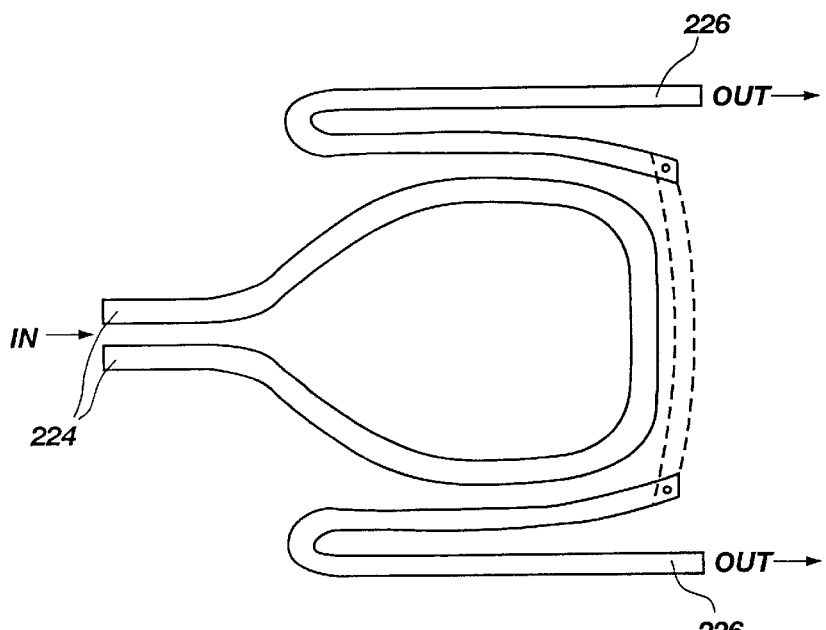
FIG. 8H is a profile view of a different 3-port coupler.

FIGS. 8F, 8G, and 8H are all embodiments of 3-port couplers. FIG. 8F shows a 3-port coupler which has a single input 216, and two outputs 218. FIG. 8G shows a single input 220 and two outputs 222. FIG. 8H shows input striplines 224, and output striplines 226.

Figure 8I:
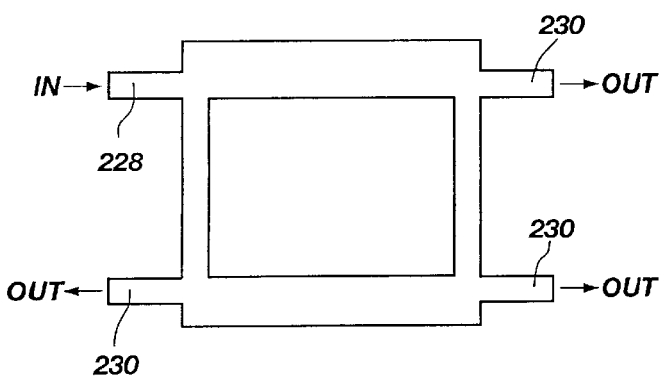
FIG. 8I is a profile view of a 4-port coupler.
Figure 8J:
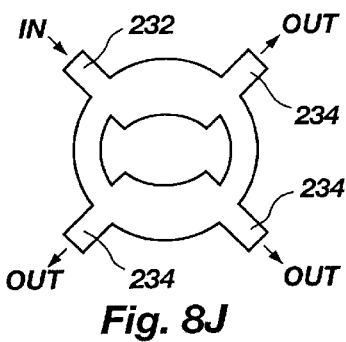
FIG. 8J is a profile view of a different 4-port coupler.
Figure 8K:
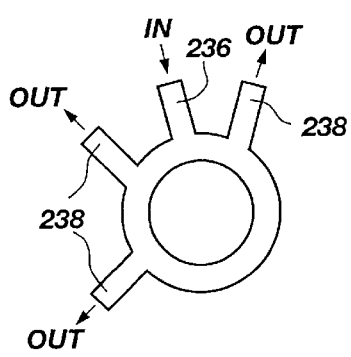
FIG. 8K is a profile view of a different 4-port coupler.
Figure 8L:
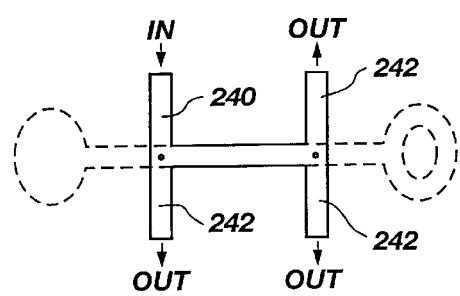
FIG. 8L is a profile view of a different 4-port coupler.
Figure 8M:
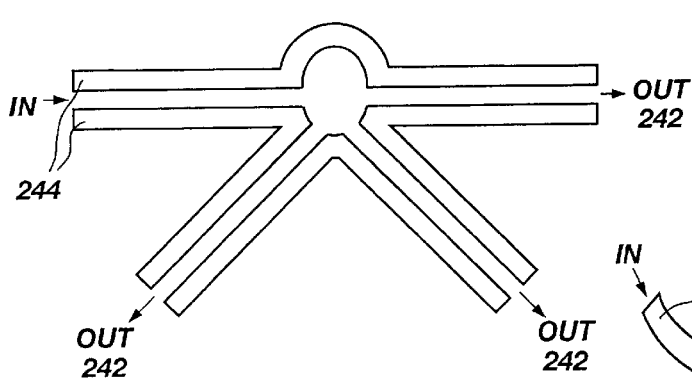
FIG. 8M is a profile view of a different 4-port coupler.
Figure 8N:
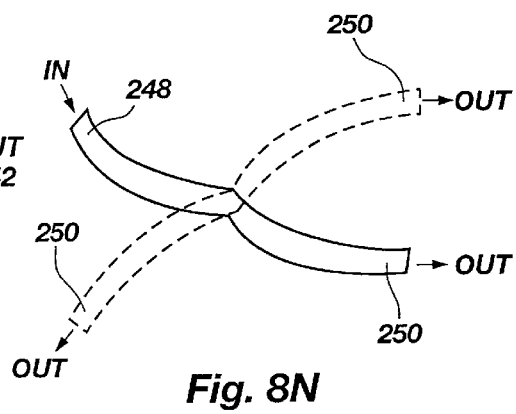
FIG. 8N is a profile view of a different 4-port coupler.

FIGS. 8I, 8J, 8K, 8L, 8M and 8N are all embodiments of 4-port couplers. FIG. 8I has a single input 228, and three outputs 230. FIG. 8J has a single input 232, and three outputs 234. FIG. 8K has a single input 236, and three outputs 238. FIG. 8L has a single input 240, and three outputs 242. FIG. 8M has a single input 244, and three outputs 246. FIG. 8N has a single input 248, and three outputs 250. FIG. 8O has a single input 322, and two outputs 324. FIG. 8P has a single input 326, and two outputs 328. FIG. 8Q has a single input 330, and two outputs 332.

An important observation to make is that all of the 2-port, 3-port and 4-port couplers shown in FIGS. 8B, 8C, 8D, 8E, 8F, 8G, 8H, 8I, 8J, 8K, 8L, 8M, 8N, 8O, 8P, and 8Q generally can be considered to have arbitrarily selected input and output ports. In other words, the inputs and outputs are generally interchangeable. However, there are often advantages for a particular selection of input and output lines because of geometry. For example, it is probably better to have the output come from an inner ring in FIG. 8B because of the shielding from stray electromagnetic signals which is naturally provided by the outer input ring.

Figure 9A:
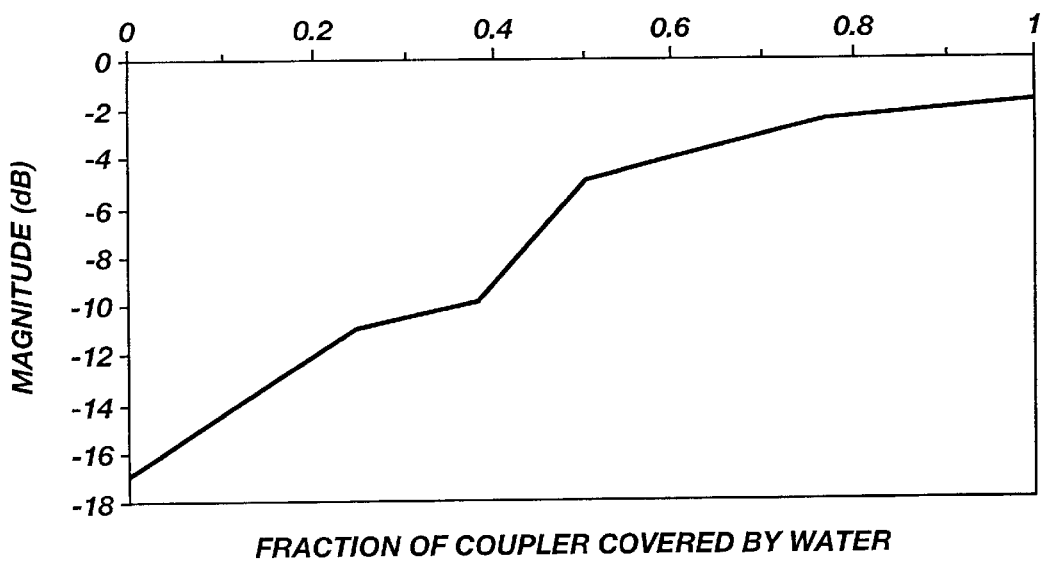
FIG. 9A is a graph showing a plot of coupling coefficient measurements. These measurements were taken using a concentric ring coupler such as the type shown in FIG. 8B. The graph shows the magnitude of coupling in decibels relative to the fraction of the coupler covered by water.

FIG. 9A is a graph showing a plot of coefficient coupling measurements. These measurements were taken using a concentric ring coupler such as the type shown in FIG. 8B. The magnitude of the coupling coefficient varies from −1.2 dB to −17.5 dB as one type of contents in a container was replaced by another type of contents. More specifically, air replaced water as water was permitted to drain from the container. The graphs provide the plots of coupling coefficient with respect to the portion or fraction of the coupler which is "covered" by water inside the container.

Figure 9B:
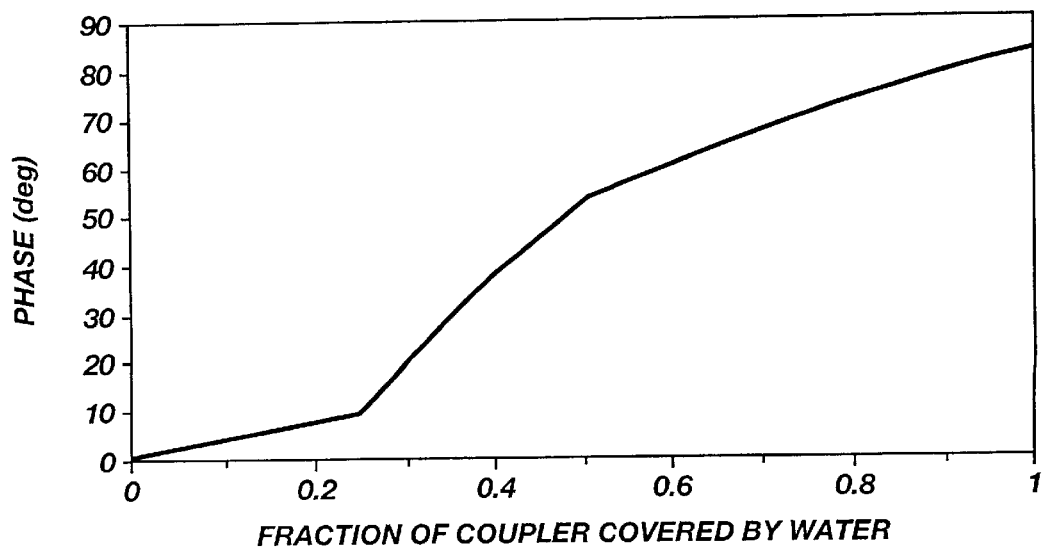
FIG. 9B is a graph showing a plot of coupling coefficient measurements. These measurements were taken using a concentric ring coupler such as the type shown in FIG. 8B. The graph shows the phase of coupling in degrees relative to the fraction of the coupler covered by water.

FIG. 9B is a graph showing a plot of coefficient coupling measurements. The phase of the coupling coefficient varies from 2 to 83 degrees relative to the source as air is replaced by water in the container.

Figure 10:
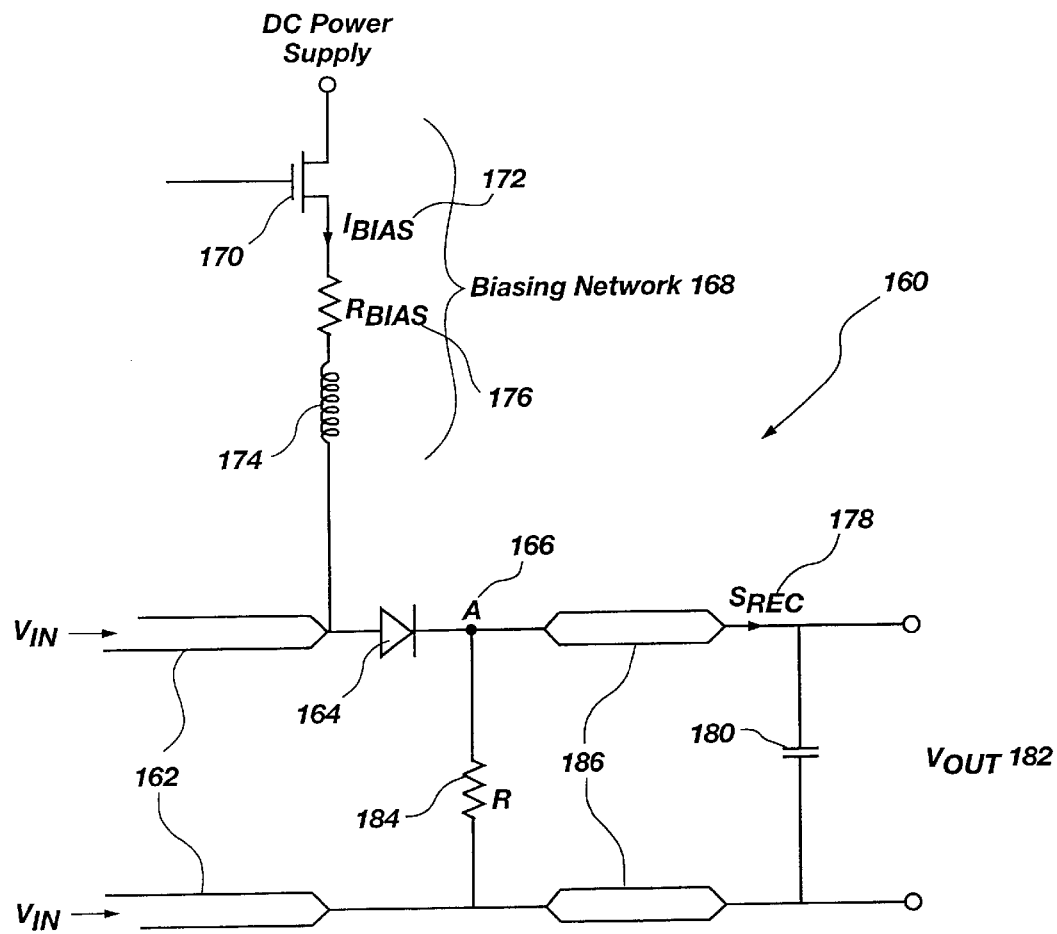
FIG. 10 is a circuit diagram showing a rectifier/integrator (R/I) circuit.

FIG. 10 is a circuit diagram showing a rectifier/integrator (R/I) circuit 160. The R/I circuit 160 shown is a presently preferred circuit for the detection circuitry 120 of FIG. 5. This R/I circuit 160 is used for measuring the degree of coupling in the sensor. This is accomplished by converting the coupled microwave signal (the output signal 156 in FIG. 8A) to a DC voltage. While a detailed description will now be provided for the circuit of FIG. 10, it should be apparent that other circuit designs can accomplish the same function, and these equivalent circuits should be considered to be within the scope of the present invention.

The input to the R/I circuit 160 is shown as V(in) 162. This input signal 162 is rectified by a diode 164. The effect is to create a time-varying DC current at point A 166. The diode 164 may be a schottky barrier diode, or any other diode that is capable of rectifying microwave frequencies. However, any diode used cannot significantly attenuate the input signal 162.

Depending upon the diode 164 which is selected, a biasing network 168 may be required. In this embodiment, the bias network 168 contains a field effect transistor (FET) 170 which is used to control bias current 172. The biasing network 168 is also used to turn off bias current 172 when the sensor system 110 is in a sleep mode. A DC blocking inductor 174 is also coupled in series with a current limiting resistor 176 to thereby provide the required bias current 172 without interfering with performance of the microwave output signal 156 which is input to the R/I circuit 160 as V(in) 162.

After the R/I circuit 160 generates a rectified signal 178, the signal 178 is integrated by a capacitor 180. The result is a steady-state DC voltage V(out) 182. Capacitor charge is slowly bled off through a resistor 184 so that the voltage across the capacitor 180 can be reduced as the strength of the sensor's output signal 156 (the input signal to the R/I circuit 160) decreases. The rate of decay is set so that V(out) 182 generally shows no ripple, but is also fast enough that V(out) 182 can accurately track the sensor system output signal 156 at V(in) 162.

In applications requiring fine temporal resolution, rapidly changing sensor output signals are important. Accordingly, the resistor 184 and the capacitor 180 can be selected to achieve the desired resolution. Advantageously, microwave sensing has time resolution which is on the order of a millionth of a second.

The capacitor 180 is essentially a short circuit to ground for microwave frequency signals. Therefore, a method is required to prevent excessive loading on the microwave circuit by the capacitor 180. One method which is often used is to use a quarter wavelength line 186 in the circuit. The result is a transformation of the zero impedance due to the capacitor 180 to an infinite impedance as seen by the diode 164. The inclusion of the quarter wavelength lines 186 does not interfere with DC signals of the detection circuit 160, so the capacitor 180 still discharges through the resistor 184. It is noted that the value of the resistor 184 is chosen so that the combined impedance of the forward-biased diode 164 and the resistor 184 will be equal to the output impedance of the sensor 114. Consequently, maximum power transfer to the capacitor 180 is achieved.

The detection circuitry 120 (FIG. 5) provides an integrated output voltage V(out) 82 (FIG. 10). The voltage V(out) 182 is then compared with a reference voltage 192. Those skilled in the art will recognize that this can be accomplished using a differential amplifier 194 as shown in FIG. 11.

Figure 11:
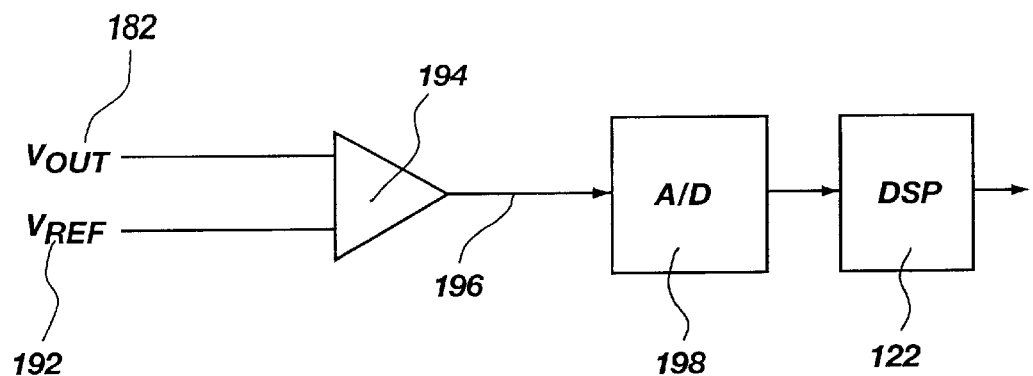
FIG. 11 is a schematic circuit/block diagram showing how a differential amplifier is used to quantify the differential output of FIG. 10.

FIG. 11 shows that in the presently preferred embodiment, an A/D converter 198 receives as an input the output 196 of the differential amplifier 194 in order to quantify the differential amplifier output 196. The output 196 from the differential amplifier 194 is a continuous voltage that is nearly proportional to the coupling coefficient of the sensor 114. A resulting digital signal from the A/D converter 198 is capable of characterizing the coupling coefficient with arbitrarily high resolution. The digital signal is transmitted to the digital signal processor 122 (FIG. 5).

The digital signal processor 122 can perform various functions. These functions include but are not limited to executing algorithms for error correction, noise filtering, signal enhancement, pattern recognition and internal calibration of digital and microwave functions. These algorithms are typically implemented using a microprocessor or a programmable gate array (FPGA).

The digital signal processor 122 is designed to provide output for alarms 124. In other words, the DSP 122 is designed to determine when an alarm condition has occurred, and to then take the appropriate action to trigger a human perceptible alarm.

The DSP 122 also receives input from the digital controller 116. In the preferred embodiment, the DSP 122 and the digital controller 116 are configured concurrently. Virtually any operating parameter of the DSP 122 can be configured as required. Configurable parameters include bias currents, linear and non-linear filtering, timing and sensor sensitivity. Filtering involves processing the digital data using programs which are written to emphasize or de-emphasize selected characteristics of the signal.

More specifically, linear low-pass filtering may be used to reduce environmental effects in some applications such as saline level detection in an IV bottle. When the bottle is bumped or tipped, bubbles and waves may wash across a sensing region where the sensor 114 is coupled to the outside of the IV bottle. With proper filtering, such disturbances will not interfere with detection of slow events like a falling fluid level.

Linear high-pass filtering may be used to increase sensitivity to rapidly occurring events. For instance, small air bubbles in a fluid line are generally more easily detectable with high-pass filtering, especially if the composition of the fluid itself is not uniform.

In addition to the low and high-pass filters, various non-linear filters may be used to eliminate the effects of noise and to enhance the sensor output signal 156. For example, a median filter is implemented to reduce impulse noise. Edge enhancement is performed to increase the sensitivity to abrupt changes in coupling.

Advantageously, linear filtered signals can also be combined with non-linear filters to provide increased sensitivity to any anticipated sensor output.

The power supply 128 of the preferred embodiment is a battery. This is owing to the portable nature, compact size, and typically low power requirements of the invention. However, because a battery is preferred, it is also desirable to monitor the voltage of the battery, and provide a means of warning a user of impending failure of the battery.

Figure 12:
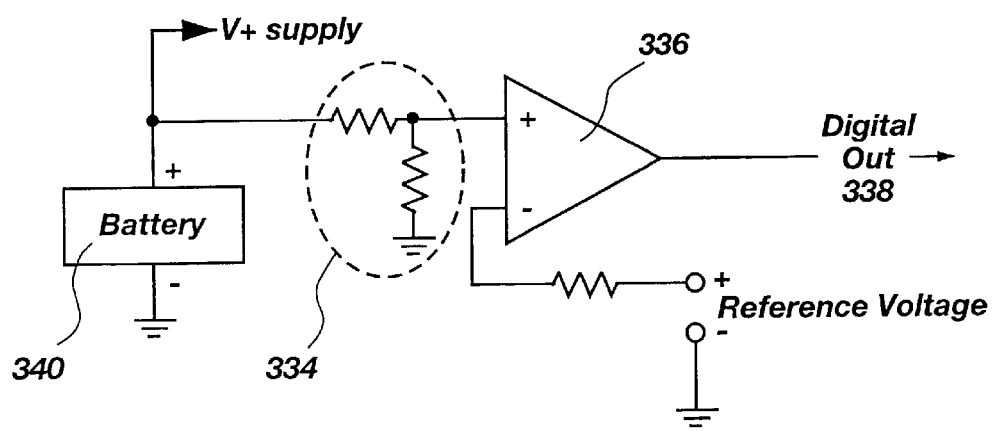
FIG. 12 is a circuit diagram which illustrates a voltage divider used in combination with a comparator to generate an alarm when the battery voltage drops below a predetermined level.

FIG. 12 shows that in the preferred embodiment, a voltage divider 334 is used in combination with a comparator 336 to thereby generate digital signals 338. The digital signals 338 are used to trigger an alarm when the voltage of the battery 340 drops below a desired voltage level, as is understood by those skilled in the art.

The alarms 124 (FIG. 5) of the present invention are preferably of two different types. These include visual and audible devices for attracting attention. However, it is possible that the sensor system 110 might not be located within the visual or audible range of a user. Therefore, the preferred embodiment also includes a data port which can signal a status of the sensor system 110 to a remote monitoring device such as a computer.

The alarm conditions of the present invention not only include a warning signal for whatever alarm condition is designed to trigger the sensor system 110 (such as a low liquid level), but also for unlikely but not impossible occurrences such as the sensor 114 becoming detached from a container or other device being monitored. To assist the user with determination of what event has triggered the alarm or alarms, the visual and audible alarms are varied. For example, a different tone or pattern of sounds can be created for the audible alarm. Likewise, a different pattern or intensity of light is used for the visual alarm.

There are several alternative embodiments for various components of the present invention described above. For example, FIG. 11 shows that an A/D converter 198 is used to generate digital signals which represent a continuous voltage that is nearly proportional to the coupling coefficient. However, instead of digitizing the output of the differential amplifier 194, the output is used to directly activate an alarm mechanism which is driven by an analog signal. For example, the analog alarm mechanism can be a visual alarm such as a light, or an audible alarm such as a buzzer. Accordingly, this alternative embodiment would also eliminate the DSP 122 because no digital signals are being generated.

A second alternative embodiment involves using a single 3-port coupler. The presently preferred embodiment describes using a 2-port coupler as shown in FIG. 8B where there is one input and one output. However, a 3-port coupler as shown in FIGS. 8F, 8G and 8H use one input path and two output paths. One of the advantages of these 3-port configurations is that it enables simultaneous sensing of container contents at multiple locations. The sensors are able to distinguish between differences in the contents at the outputs. Accordingly, each output is characterized by its own coupling coefficient.

A 3-port coupler and its associated circuitry provide a high common mode rejection ratio (CMRR). A high CMRR results in a type of sensing that ignores everything but the difference between the coupling coefficient on each side of the coupler. In practical terms, this means that CMRR is a measure of insensitivity of the sensor to environmental interference, manufacturing variations, and anything else that can influence all regions of the sensor equally.

Figure 13:
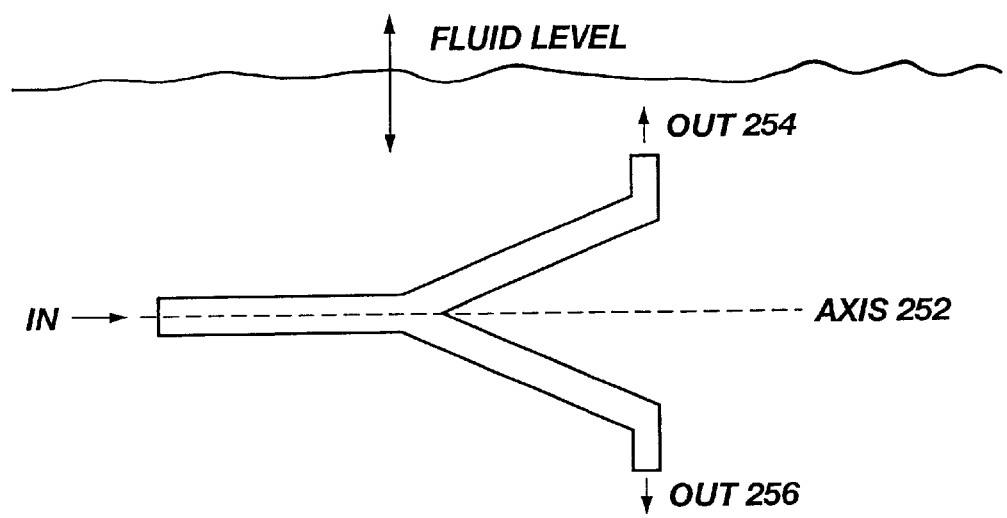
FIG. 13 is a profile view of a 3-port coupler on a container wall using a difference between signals from outputs to determine a liquid level.

A 3-port coupler is ideal for level sensing in a container when oriented as shown in FIG. 13. What will occur using this particular design is that when the level of the contents (a fluid) reaches the axis 252, the difference between the two output signals 254, 256 is maximized. Generally, this will be the alarm condition which results in the activation of a human perceptible alarm.

Figure 14:
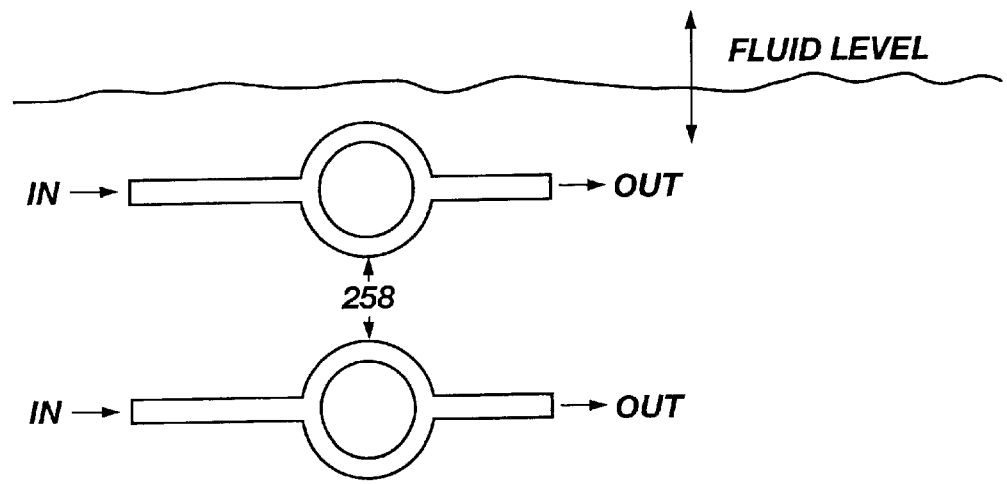
FIG. 14 is a profile view of two 2-port couplers on a container wall using a difference between signals from outputs to determine a liquid level.

Another alternative embodiment of the present invention involves replacing the 3-port coupler used in FIG. 13 with two 2-port couplers as shown in FIG. 14. Whereas the 3-port coupler has a fixed spacing between outputs, the spacing 258 between two independent 2-port couplers can be arbitrary so as to meet specific needs of more applications.

In another alternative embodiment, level sensing of a container's contents can also be achieved using a single 2-port coupler having dimensions designed to form a balanced bridge. This type of coupler produces constructive interference and a strong output signal at the output port when the sensor is adjacent to fluid, and destructive interference when the sensor is adjacent to the fluid-air boundary. It should also be apparent that the interference can also be reversed depending upon whether the sensor is adjacent to fluid or the fluid-air boundary.

What is important to realize is that a coupler's dimensions allow for the creation of sensors which are sensitive to the fluid-air boundary, or to any other property which the sensors are able to detect. The sensors may be resonant or non-resonant at the sensing frequency. Sub-resonant couplers, those smaller than half a wavelength, may be used to reduce sensor size. This makes it possible to offer different sensor configurations for different applications, without having to modify the supporting circuitry. However, a sensor with a single 2-port coupler has the advantage of requiring simpler interconnections between the sensor and the supporting circuitry than sensors with two couplers or with a single multi-port coupler.

Figure 15:
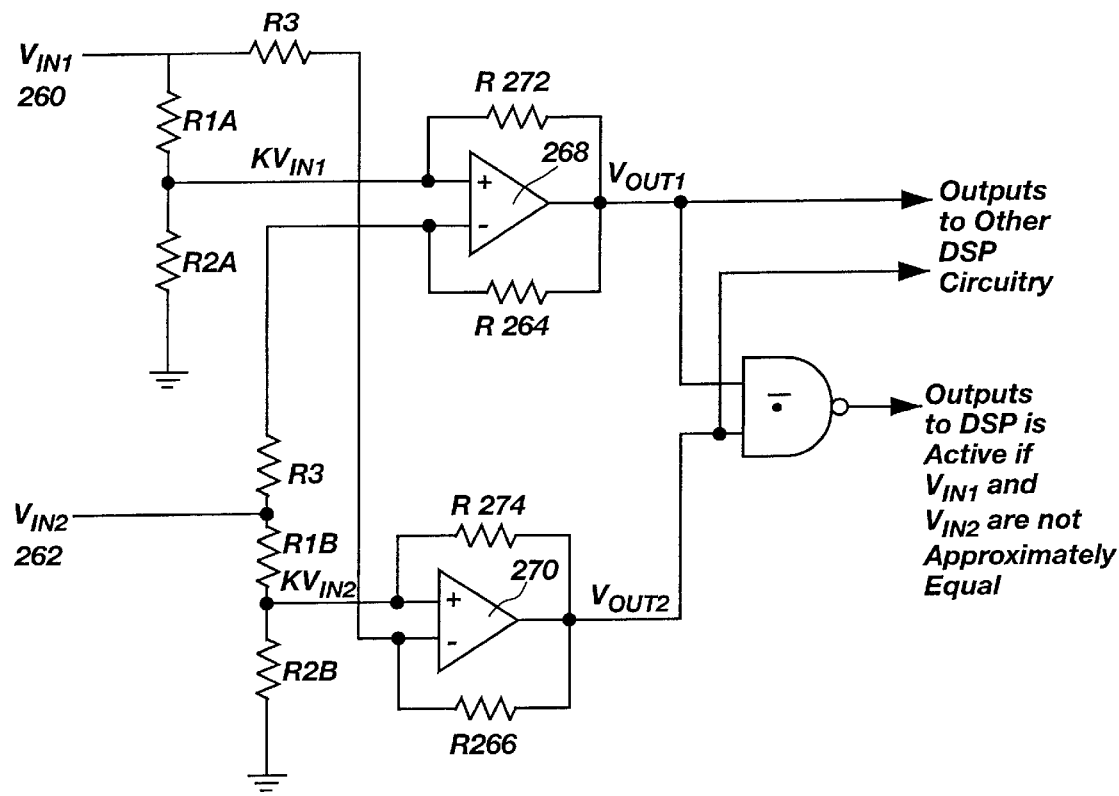
FIG. 15 is schematic diagram of a differential amplifier circuit used to achieve a high common mode rejection ratio, where two output signals are compared to determine if the signals are approximately equal or not, and where the circuit sensitivity is adjustable.

When a 3-port coupler is being used, the present invention requires a differential amplifier circuit in order to achieve high CMRR. An example of such a detector circuit is shown in FIG. 15. This circuit includes an equality detector. Specifically, each of the two outputs from the 3-port coupler are rectified and integrated using the circuit shown in FIG. 10. The integrated output signals V(in1) 260 and V(in2) 262 are compared to determine if the digital signal processing circuitry 122 (FIG. 5) will trigger an alarm.

The gain of amplifiers 268 and 270 is controlled by resistors R264 and R266, respectively. Hysteresis is controlled by resistors R272 and R274. Advantageously, it is possible to tune each side of the amplifiers 268 and 270 separately to thereby compensate for component and environmental variations. For example, reducing the value of R272 will increase hysteresis when voltage level V(in1) 260 drops below V(in2) 262. Resistor R274 has the same affect on hysteresis when V(in1) 260 rises above V(in2) 262.

The amplifiers 268 and 270 will trigger the digital circuitry which follows this circuit when V(in1) 268 and V(in2) 270 are not approximately equal. The ratio R2/(R1+R2) is adjusted to define just how close V(in1) 260 and V(in2) 262 must be to be considered equal. Accordingly, R1A, R2A, R1B and R2B are selected on each side of the amplifiers 268 and 270 to create a desired margin of equality. This margin of equality is represented by the factor K in FIG. 15. R3 is selected so as to marginally attenuate the input signals 260 and 262.

Because it is possible to independently control parameters for each side of the amplifiers 268 and 270, sensing may be made symmetrical or asymmetrical as desired. If sensing is to be symmetrical, orientation of the sensor on a container is less critical. In other words, the sensor may be placed upside down on the side of a container without affecting sensitivity or reliability. Of course, this may not be necessary if the circuitry 112 hangs from the sensor 114, thus naturally orienting the sensor.

A differential detection scheme as explained above could also be used to compare the electrical loading of the sensor on a container wall to a pre-defined reference load by using a second differential amplifier. If the output signals from both sensors are approximately equal and both sensors indicate a load characteristic of a detached sensor, an alarm is activated to inform the user that the sensor has become detached from the container wall, and thus requires repositioning. Therefore, the advantages of differential sensing (because of a high CMRR) are realized for the detached alarm condition as well.

An alternate differential sensing scheme is possible with 3-port sensors or with two identical 2-port sensors. The output ports of the coupler or couplers connect directly to the differential inputs of the amplifier circuitry. Amplifier components are chosen and arranged to enable operation at the sensing frequency. The output of the amplifier is then rectified and integrated to produce a signal which indicates the presence or absence of fluid. By reversing the order of the differential amplifier and the R/I circuits, variations in phase and amplitude of the coupled signals can be detected. The advantages of CMRR are still realized with this scheme.

The basic sensor configurations, a few of which were shown in the examples above in FIGS. 8B to 8Q, can also be adapted to other situations. For example, two independent amplifiers 268 and 270 (FIG. 15) can be used to detect flow rate and direction of air in fluid lines, as well as the size of an air bubble. This is determined by coupling V(out1) and V(out2) (FIG. 15) to the DSP circuitry.

Figure 16:
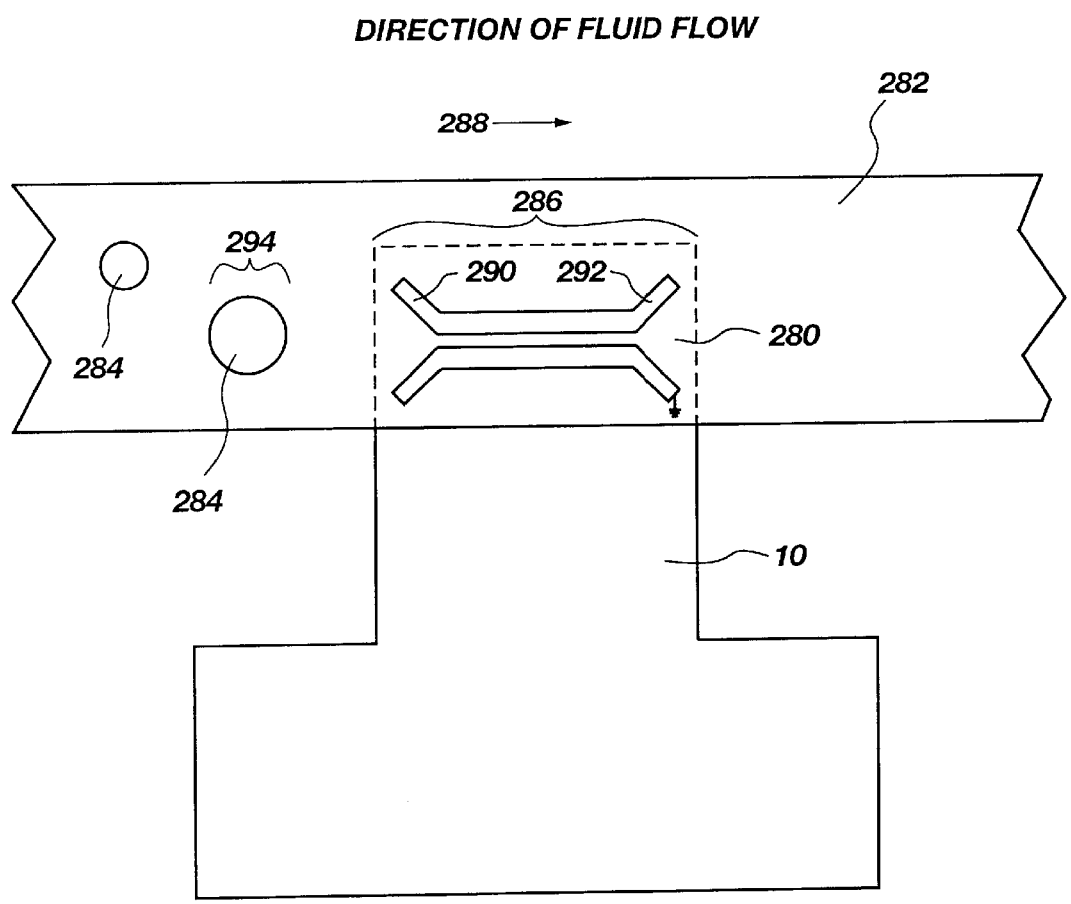
FIG. 16 is a profile view of a sensor being attached to a tube structure and being used to determine characteristics of a fluid and the fluid flow.

The situation being described is illustrated in FIG. 16. A 3-port coupler (sensor) 280 is shown attached to a tube 282 which has fluid flowing therein. Within the fluid are air bubbles 284. Now it can be seen that a difference in time between signal events (expressed as the time 286 it takes for an air bubble 284 to cross in front of both output sensors) at V(out1) and V(out2) (see FIG. 15) determines the flow velocity of the fluid in the tube 282. The order of signal events determines flow direction. For the fluid flow to be in the direction indicated by arrow 288, the first event will be when an air bubble 284 crosses in front of output sensor 290, and the second event will be when the air bubble 284 crosses in front of the output sensor 292.

Finally, the duration of the events is used to determine the bubble size. In other words, an event in front of a single sensor will last as long as it takes the air bubble 284 to completely cross in front of a sensor. This is expressed as the time it takes the air bubble 284 to travel a distance which is approximately equal to its diameter 294.

In addition to being able to make hardware modifications to the sensor system 110 for adjustment of parameters such as sensitivity and hysteresis, the DSP 122 (FIG. 5) is configurable through software. Therefore, many variations of the embodiments described above are possible without altering the hardware.

Some examples of possible applications which can be implemented are the identification of bubble patterns or other inconsistencies in fluids transported through fluid lines. This function is most likely to be used when the overall system response relies on different stimuli. For example, the device can sense flow rates in a fluid line as determined by detection of small bubbles, but still be capable of triggering an alarm if larger bubbles are detected. An alarm can also be triggered if the flow of the fluid reverses.

Figure 17:
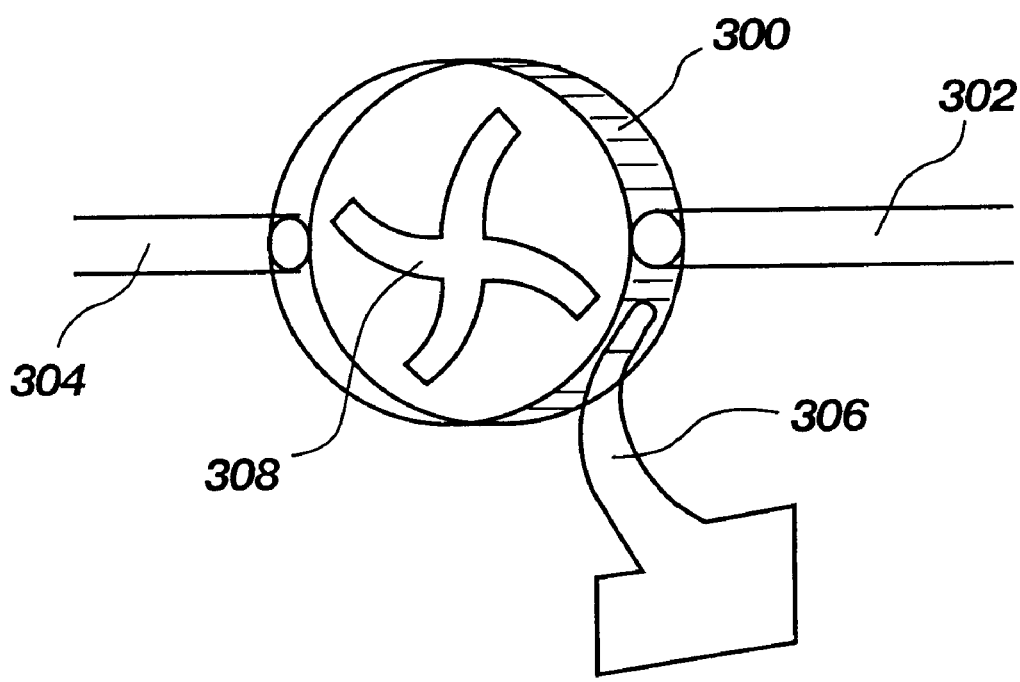
FIG. 17 is a cut-away perspective view of a sensor coupled to a pump housing and which can determine characteristics of the pump housing contents and of the pump itself.

One such use of pattern detection is shown in FIG. 17. A pump housing 300 is shown with an inlet tube 302 and an outlet tube 304. The sensor system 306 is shown coupled to the pump housing 300. The sensor system 306 is not only capable of identifying the contents within the pump housing 300, but it can also monitor the speed of the pump, detect variations in the fluid (caused by air, contamination, occlusions, etc.) and even detect wear or damage to the propeller 308.

The DSP can also be configured so as to save sensor signals from a known substance, and then make comparisons to received signals so as to non-invasively detect changes in the properties of the substance. This ability can be applied to such applications as analysis of substance purity, leakage detection in soil surrounding underground storage tanks, or proximity of a substance to a sensor.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A sensor system for use in characterizing contents of a container, wherein said sensor system analyzes microwave frequency electromagnetic signals generated therefrom to thereby determine characteristics of the container contents, said system comprising:

an electromagnetic sensor which is disposable on a container, and which is capable of transmitting the microwave frequency electromagnetic signals, wherein the electromagnetic sensor is a microwave frequency multi-port coupler which includes an input port and at least two output ports, wherein a high common mode rejection ratio is used to thereby reduce electromagnetic sensor activity by having a first output port and a second output port;

a detector circuit which is electrically coupled to the electromagnetic sensor to thereby detect the perturbations in the microwave frequency electromagnetic signals, and which processes each signal from the first and the second output ports by rectifying, integrating, and then comparing the rectified and integrated signals using a differential amplifier circuit;

a processing device which is electrically coupled to the electromagnetic sensor, wherein the processing device develops the microwave frequency electromagnetic signals to be transmitted, analyzes the transmitted microwave frequency electromagnetic signals to thereby detect perturbations therein, and provide a human perceptible alarm when the detected perturbations indicate that an alarm condition is met;

wherein the processing device includes an oscillator which is electrically coupled to the electromagnetic sensor, and which develops the microwave frequency electromagnetic signals for transmission therefrom;

a controller for activating the oscillator and the detector circuit when the electromagnetic sensor is in a sensing mode, and for deactivating the oscillator and the detector circuit when the sensor system is in a sleep mode, and wherein a duration of the sensing and the sleep modes is programmable; and a power supply for supplying electrical current to the sensor system.

2. The sensor system as defined in claim 1 wherein the differential amplifier circuit includes:

a first operational amplifier which has coupled at a first positive terminal a first voltage divider which divides a first signal from the first output port, and which is also coupled to a first resistor which modifies hysteresis, said operational amplifier also being coupled at an output port to an opposite side of the first resistor, and to a second resistor which modifies a gain of the first operational amplifier, said operational amplifier also being coupled at a negative terminal to an opposite side of the second resistor, and to a third resistor which attenuates a second signal from the second output port;

a second operational amplifier which has coupled at a second positive terminal a second voltage divider which divides the second signal from the second output port, and which is also coupled to a fourth resistor which modifies hysteresis, said operational amplifier also being coupled at an output port to an opposite side of the fourth resistor, and to a fifth resistor which modifies a gain of the second operational amplifier, said operational amplifier also being coupled at a negative terminal to an opposite side of the fifth resistor, and to a sixth resistor which attenuates the first signal from the first output port; and wherein the output ports of the first and the second operational amplifiers are compared to determine if they are approximately equal.

3. The sensor system as defined in claim 1 wherein the processing device is further comprised of:

a digital signal processor (DSP) which is electrically coupled to the detector circuit, wherein the DSP filters data received therefrom so as to determine whether at least one alarm condition is met, and which transmits a signal if it is determined that the at least one alarm condition is met; and a human perceptible alarm which is electrically coupled to the DSP for receiving the signal indicating that the at least one alarm condition is met, and which activates the human perceptible alarm.

4. The sensor system as defined in claim 1 wherein the processing device further comprises an analog driven human perceptible alarm which is electrically coupled to the detector circuit, and which receives a signal indicating that the at least one alarm condition is met, and which activates the analog driven human perceptible alarm in response to receiving the signal.

5. The sensor system as defined in claim 3 wherein the processing device is further comprised of a data output port so that the signal indicating that the at least one alarm condition is met can be transmitted to a remote location.

6. The sensor system as defined in claim 1 wherein the perturbations are manifested as a compression of electromagnetic fields generated by the microwave frequency electromagnetic sensor.

7. The sensor system as defined in claim 1 wherein the electromagnetic sensor is coupled to the container by an adhesive which binds a sensing surface of the electromagnetic sensor generally flush against the container.

8. The sensor system as defined in claim 1 wherein the system further comprises:

a plurality of output ports on the microwave frequency electromagnetic sensor; and a plurality of detector circuits, wherein each of the plurality of detector circuits is coupled to a corresponding one of the plurality of output ports to thereby enable the sensor system to simultaneously detect different alarm conditions.

9. The sensor system as defined in claim 1 wherein the input port is interchangeable with at least one of the at least one output ports.

10. The sensor system as defined in claim 1 wherein the microwave frequency multi-port coupler is a 4-port microwave frequency coupler.

11. The sensor system as defined in claim 10 wherein the microwave frequency multi-port couplers which are suitable as the microwave frequency electromagnetic sensor are formed on generally planar surfaces as stripline traces.

12. The sensor system as defined in claim 11 wherein the microwave frequency multi-port couplers are configured in a direct coupling or parallel coupling arrangement.

13. The sensor system as defined in claim 1 wherein the oscillator further comprises an oscillating transistor having a common-base bipolar configuration, and which utilizes feedback to tune the oscillator to a desired microwave frequency.

14. The sensor system as defined in claim 13 wherein the system further comprises the oscillator having an output impedance which generally matches an input impedance of the microwave frequency electromagnetic sensor to thereby obtain maximum power transfer therebetween.

15. The sensor system as defined in claim 13 wherein the oscillating transistor is biased via a direct current (DC) voltage through a current limiting resistor and a microwave frequency blocking inductor.

16. The sensor system as defined in claim 13 wherein the controller controls the sensing mode and the sleeping mode through a power supply transistor which is caused to provide bias current to the oscillating transistor when in sensing mode, and which is caused to terminate the bias current to the oscillating transistor when in sleeping mode.

17. The sensor system as defined in claim 1 wherein the detector circuit is comprised of:
 a rectifying circuit which is electrically coupled to the at least one output port to thereby receive and rectify the output signal; and
 an integrating circuit which is electrically coupled to an output of the rectifying circuit and which integrates the rectified output signal to thereby develop an output voltage which is proportional to an integral of the output signal, and which is a measure of a degree of coupling in the microwave frequency electromagnetic sensor.

18. The sensor system as defined in claim 17 wherein the rectifying circuit is comprised of:
 a diode which when forward biased enables the output signal to be rectified to thereby create a time-varying DC current, and which is capable of operating at microwave frequencies; and
 a biasing network which is electrically coupled to an input of the diode and which causes the diode to be forward biased when the sensor system is in the sensing mode.

19. The sensor system as defined in claim 18 wherein the detector circuit further comprises:
 the integrator which is comprised of a capacitor for generating a steady-state DC output voltage; and
 a length of conductor between an output of the diode and the capacitor, wherein the length of the conductor is a quarter wavelength of the microwave frequency electromagnetic signals, so that a zero impedance of the capacitor to microwave frequencies is transformed to an infinite impedance as seen by the diode.

20. The sensor system as defined in claim 19 wherein the detector circuit further comprises a resistor coupled to the diode output and ground which bleeds off a charge on the capacitor so that a voltage across the capacitor can be reduced as strength of the output signal from the microwave frequency electromagnetic sensor decreases.

21. The sensor system as defined in claim 20 wherein the detector circuit further comprises the resistor having a value that when combined with an impedance of the diode, a combined diode and resistor impedance is generally equal to an output impedance of the microwave frequency electromagnetic sensor.

22. The sensor system as defined in claim 21 wherein the detector circuit further comprises a differential amplifier which is electrically coupled to the integrator and a reference voltage, and which receives as inputs the voltage across the capacitor of the integrator, and a reference voltage.

23. The sensor system as defined in claim 22 wherein the detector system further comprises an analog-to-digital (A/D) converter which is electrically coupled to the differential amplifier and which receives as input an output signal therefrom.

24. The sensor system as defined in claim 23 wherein the detector system further comprises the DSP which is electrically coupled to the A/D convertor and which receives as an input signal an output signal therefrom.

25. The sensor system as defined in claim 24 wherein the DSP is a programmable device for executing at least one algorithm to accomplish error correction, noise filtering, signal enhancement, pattern recognition and internal calibration.

26. The sensor system as defined in claim 24 wherein the DSP further comprises filters for executing low-pass filtering, high-pass filtering, non-linear filtering and combinations thereof to enable reduction of environmental effects, microwave frequency electromagnetic sensor sensitivity, liquid level detection, noise reduction, edge enhancement, and increased sensitivity to anticipated electromagnetic sensor output.

27. The sensor system as defined in claim 24 wherein the DSP is electrically coupled to a human perceptible alarm system capable of generating different alarms for different alarm conditions, wherein the human perceptible alarm system receives input signals from the DSP which indicate when an alarm condition exists, and what type of alarm condition exists.

28. A method for characterizing contents of a container using a sensor system, wherein said method includes analyzing microwave frequency electromagnetic signals which are generated by an electromagnetic sensor to thereby determine characteristics of the container contents, said method comprising the steps of:
 (1) disposing the electromagnetic sensor, which is capable of transmitting the microwave frequency electromagnetic signals, on a container;
 (2) developing the microwave frequency electromagnetic signals in a processing device which is electrically coupled to the electromagnetic sensor, and transmitting said signals from the electromagnetic sensor, wherein the microwave frequency electromagnetic signals are generated utilizing an oscillator which is electrically coupled to the electromagnetic sensor;
 (3) utilizing a detector circuit which is electrically coupled to the electromagnetic sensor to thereby detect the perturbations in the microwave frequency electromagnetic signals;
 (4) activating the oscillator and the detector circuit when the electromagnetic sensor is in a sensing mode;
 (5) analyzing the transmitted microwave frequency electromagnetic signals to thereby detect perturbations therein;
 (6) utilizing at least a 3-port coupler as the microwave frequency electromagnetic sensor, wherein the 3-port coupler has a first output port and a second output port, and wherein the detector circuit processes each signal from the first and the second output ports of the 3-port coupler by rectifying, integrating, and then comparing the rectified and integrated signals from the first and the second output ports using a differential amplifier circuit which amplifies any difference between each signal, wherein the sensor system has a high common mode rejection ratio to thereby reduce sensor system sensitivity, and wherein the detector circuit will minimize an influence of external factors so that the detector circuit can determine whether an alarm condition exists;

(7) providing a human perceptible alarm when the detected perturbations indicate that an alarm condition is met; and (8) deactivating the oscillator and the detector circuit when the sensor system is in a sleep mode.

29. The method as defined in claim 28 wherein the method further comprises the step of programming a duration of the sensing modes and the sleep modes to thereby limit energy consumption when the sensor is used as a stand-alone device.

30. The method as defined in claim 28 wherein the method further comprises the steps of:

(1) filtering data from the detector circuit through a digital signal processor (DSP) so as to determine whether at least one alarm condition is met;

(2) transmitting a signal from the DSP if it is determined that the at least one alarm condition is met; and (3) generating a human perceptible alarm in response to the signal from the DSP, thereby indicating that the at least one alarm condition is met.

31. The method as defined in claim 28 wherein the method further comprises the step of activating an analog driven human perceptible alarm directly from the detector circuit when the detector circuit determines that at least one alarm condition is met.

32. The method as defined in claim 30 wherein the method further comprises the step of transmitting the signal indicating that the at least one alarm condition is met to a remote location.

33. The method as defined in claim 28 wherein the step of detecting perturbations more specifically comprises the step of detecting a compression of electromagnetic fields generated by the microwave frequency electromagnetic sensor, wherein a degree of compression indicates properties of the contents.

34. The method as defined in claim 28 wherein the method further comprises the step of coupling the electromagnetic sensor to the container by an adhesive which binds a sensing surface of the electromagnetic sensor generally flush against the container.

35. The method as defined in claim 28 wherein the method further comprises the step of interchanging the input port with the at least one output port when desired.

36. The method as defined in claim 28 wherein the method further comprises the step of selecting the microwave frequency multi-port coupler from the group of microwave frequency multi-port couplers including 2-port, 3-port and 4-port microwave frequency couplers.

37. The method as defined in claim 36 wherein the method further comprises the step of configuring the microwave frequency multi-port couplers in a direct coupling or parallel coupling arrangement.

38. The method as defined in claim 28 wherein the method further comprises the step of generating microwave frequencies utilizing a transistor having adjustable feedback to modify the microwave frequency being generated.

39. The method as defined in claim 38 wherein the method further comprises the step of biasing the transistor via a direct current (DC) voltage through a current limiting resistor and a microwave frequency blocking inductor.

40. The method as defined in claim 38 wherein the method further comprises the step of controlling the sensing mode and the sleeping mode through a power supply transistor which is caused to provide bias current to the transistor when in sensing mode, and which is caused to terminate the bias current to the transistor when in sleeping mode.

41. The method as defined in claim 28 wherein the method further comprises the steps of:

(1) rectifying a signal from the at least one output port to thereby create a signal having a time-varying DC current; and (2) integrating the signal having the time-varying DC current to thereby develop an output voltage which is proportional to an integral of the output signal, and which is a measure of a degree of coupling in the microwave frequency electromagnetic sensor.

42. The method as defined in claim 41 wherein the method further comprises the steps of:

(1) rectifying the signal from the at least one output port through a diode which is forward biased and operates at microwave frequencies; and (2) forward biasing the diode when the sensor system is in the sensing mode.

43. The method as defined in claim 42 wherein the method further comprises the steps of:

(1) integrating the time-varying DC signal using a capacitor to thereby generate a steady-state DC output voltage; and (2) preventing excessive loading on the sensor system by inserting a length of conductor between an output of the diode and the capacitor which is a quarter wavelength of the microwave frequency electromagnetic signals, so that a zero impedance of the capacitor to microwave frequencies is transformed to an infinite impedance as seen by the diode.

44. The method as defined in claim 43 wherein the method further comprises the step of bleeding off a charge on the capacitor so that a voltage across the capacitor can be reduced as strength of the output signal from the microwave frequency electromagnetic sensor decreases.

45. The method as defined in claim 44 wherein the method further comprises the step of matching an output impedance of the electromagnetic sensor with an input impedance of the detector circuit by selecting the resistor to have a value which when combined with an impedance of the diode results in the input impedance being generally equal to the output impedance of the microwave frequency electromagnetic sensor.

46. The method as defined in claim 45 wherein the method further comprises the step of obtaining a signal which is generally proportional to a coupling coefficient of the electromagnetic sensor by electrically coupling a differential amplifier to the integrator and a reference voltage so that the differential amplifier receives as inputs the voltage across the capacitor of the integrator, and a reference voltage.

47. The method as defined in claim 46 wherein the method further comprises the step of generating a digital output signal representative of the coupling coefficient by electrically coupling an analog-to-digital (A/D) converter to the differential amplifier.

48. The method as defined in claim 47 wherein the method further comprises the step of digitally processing the digital output signal from the A/D converter using a digital signal processor to thereby accomplish error correction, noise filtering, signal enhancement, pattern recognition and internal calibration.

49. The method as defined in claim 48 wherein the method further comprises the steps of:

(1) filtering the digital output signal from the A/D converter utilizing low-pass filtering to reduce environmental effects and to modify electromagnetic sensor sensitivity;

(2) filtering the digital output signal from the A/D converter utilizing high-pass filtering to increase sensitivity to rapidly occurring events; and (3) filtering the digital output signal from the A/D converter utilizing non-linear filtering and combinations of low-pass, high-pass and non-linear filtering to enable liquid level detection, edge enhancement, and increased sensitivity to anticipated electromagnetic sensor output.

50. The method as defined in claim 48 wherein the method further comprises the step of generating a selectable human perceptible alarm depending upon which alarm condition is indicated as being received from the digital signal processor.

51. The method as defined in claim 50 wherein the method further comprises the step of simultaneously checking for a plurality of different alarm conditions, all of which can trigger an alarm event, by providing a plurality of output ports on the electromagnetic sensor.

52. The method as defined in claim 51 wherein the method further comprises the step of generating a plurality of different human perceptible alarms, each of which is indicative of a different alarm condition.

53. The method as defined in claim 46 wherein the method further comprises the step of (quantifying) selecting the coupling coefficient (using the following equation) to be:

$$c = 10 \log\left|\frac{p(\text{in})}{p(\text{out})}\right|, \emptyset(\text{out}) - \emptyset(\text{in})$$

where p(in) is a magnitude and Ø(in) is a phase of input power, and p(out) and Ø(out) are a measurable output power and phase, respectively.

* * * * *